United States Patent
Goossen et al.

(10) Patent No.: US 11,518,756 B2
(45) Date of Patent: Dec. 6, 2022

(54) ARYLATION METHOD

(71) Applicant: UMICORE AG & CO. KG, Hanau-Wolfgang (DE)

(72) Inventors: Lukas J. Goossen, Bochum (DE); Matthias Gruenberg, Wuppertal (DE)

(73) Assignee: UMICORE AG & CO. KG, Hanau-Wolfgang (DE)

( * ) Notice: Subject to any disclaimer, the term of this patent is extended or adjusted under 35 U.S.C. 154(b) by 124 days.

(21) Appl. No.: 15/779,563

(22) PCT Filed: Dec. 1, 2016

(86) PCT No.: PCT/EP2016/079486
§ 371 (c)(1),
(2) Date: May 29, 2018

(87) PCT Pub. No.: WO2017/093427
PCT Pub. Date: Jun. 8, 2017

(65) Prior Publication Data
US 2020/0031803 A1 Jan. 30, 2020

(30) Foreign Application Priority Data

Dec. 2, 2015 (EP) .................... 15197483

(51) Int. Cl.
| | | |
|---|---|---|
| *C07D 403/12* | (2006.01) | |
| *C07D 209/08* | (2006.01) | |
| *C07D 209/14* | (2006.01) | |
| *C07D 401/12* | (2006.01) | |
| *C07D 405/12* | (2006.01) | |
| *C07D 409/12* | (2006.01) | |
| *C07C 211/61* | (2006.01) | |

(52) U.S. Cl.
CPC .......... *C07D 403/12* (2013.01); *C07C 211/61* (2013.01); *C07D 209/08* (2013.01); *C07D 209/14* (2013.01); *C07D 401/12* (2013.01); *C07D 405/12* (2013.01); *C07D 409/12* (2013.01)

(58) Field of Classification Search
CPC .. C07D 403/12; C07D 209/08; C07D 209/14; C07D 401/12; C07D 405/12; C07D 409/12
See application file for complete search history.

(56) References Cited

U.S. PATENT DOCUMENTS

| | | |
|---|---|---|
| 8,865,322 B2 | 10/2014 | Yi et al. |
| 9,478,753 B2 | 10/2016 | Jung et al. |
| 2008/0255389 A1 | 10/2008 | Coggan et al. |
| 2012/0068170 A1* | 3/2012 | Pflumm ............... C07D 413/04 257/40 |
| 2013/0069049 A1* | 3/2013 | Park .................... C07D 487/04 257/40 |
| 2016/0257650 A1 | 9/2016 | Goossen et al. |

FOREIGN PATENT DOCUMENTS

| | | |
|---|---|---|
| CN | 102372661 A | 3/2012 |
| EP | 2 407 502 A1 | 1/2012 |
| EP | 2 421 064 A2 | 2/2012 |
| EP | 3 109 253 A1 | 12/2016 |
| JP | 2012-025745 A | 2/2012 |
| JP | 2014-111552 | 6/2014 |
| KR | 2012119881 A * | 10/2012 |
| TW | 201522282 A | 6/2015 |
| WO | 2013/060418 A1 | 5/2013 |
| WO | 2015/059049 A1 | 4/2015 |
| WO | 2015/102118 | 7/2015 |

OTHER PUBLICATIONS

Hamann et al. J. Am. Chem. Soc. 1998, 120, 7369-7370 (Year: 1998).*
Hagopian et al. Journal of Organometallic Chemistry 2006, 691, 4890-4900 (Year: 2006).*
Thayumanavan et al. Chem. Mater. 1997, 9, 3231-3235 (Year: 1997).*
Schlummer et al. Adv. Synth. Catal. 2004, 346, 1599-1626 (Year: 2004).*
Harris et al. J. Org. Chem. 2000, 65, 5327-5333 (Year: 2000).*
International Search Report dor PCT/EP2016/079486, dated Jun. 8, 2017 in English Language.
Written Opinion of the International Searching Authority dated Jun. 8, 2017 for International Patent Application No. PCT/EP2016/079486 (18 pages in German with English translation).
International Preliminary Report on Patentability dated Jun. 5, 2018 for International Patent Application No. PCT/EP2016/079486 (19 pages in German with English translation).
Pompeo, M., et al. Pd-PEPPSI-IPent$^{Cl}$: A Highly Effective Catalyst for the Selective Cross-Coupling of Secondary Organozinc Reagents. Angewandte Chemie [Applied Chemistry], International Edition. 2012, vol. 51, pp. 11354-11357.
Pompeo, M., et al. Room-Temperature Amination of Deactivated Aniline and Aryl Halide Partners with Carbonate Base Using a Pd-PEPPSI-IPent$^{Cl}$-o-Picoline Catalyst. Angewandte Chemie, [Applied Chemistry], International Edition, 2014, vol. 53, pp. 3223-3226.
Hamann, B.C., et al. Sterically Hindered Chelating Alkyl Phosphines Provide Large Rate Accelerations in Palladium-Catalyzed Amination of Aryl Iodides, Bromides, and Chlorides, and the First Amination of Aryl Tosylates, Journal of the American Chemical Society, American Chemical Society. 1998. vol. 120, pp. 7369-7370.
Hartwig, J. F. Evolution of a Fourth Generation Catalyst for the Amination and Thioetherification of Aryl Halides. Accounts of Chemical Research. 2008. vol. 41, No. 11, pp. 1534-1544.
Zhang Y., et al.: Buchwald-Hartwig Amination of (Hetero)Aryl Tosylates Using a Well-Defined N-Heterocyclic Carbene/Palladium(II) Precatalyst. The Journal of Organic Chemistry. 2015. vol. 80, No. 15, pp. 7666-7673.

(Continued)

*Primary Examiner* — Matthew P Coughlin
(74) *Attorney, Agent, or Firm* — Smith, Gambrell & Russell, LLP

(57) ABSTRACT

The present invention relates to a selective method for carrying out the Buchwald-Hartwig coupling of biphenyl derivatives.

12 Claims, No Drawings

(56) References Cited

OTHER PUBLICATIONS

Monguchi, Y., et al. Evaluation of Aromatic Amination Catalyzed by Palladium on Carbon: A Practical Synthesis of Triarylamines. Advanced Synthesis & Catalysis. 2008, vol. 350, No. 17, pp. 2767-2777.
Demi, S., et al. Synthesis and characterization of bidentate NHC-Pd complexes and their role in amination reactions. Polyhedron, 2011, vol. 30, pp. 195-200.
Grünberg, M. F., et al. Selective Monoarylation of Primary Anilines Catalyzed be Pd(dippf) and its Application in OLED Component Synthesis. Advanced Synthesis & Catalysis. 2016. vol. 358, No. 10, pp. 1589-1594.
Hoi, K. H., et al. Amination with Pd-NHC Complexes: Rate and Computational Studies Involving Substituted Aniline Substrates. Chem. Eur. J.. 2012. vol. 18, pp. 145-151.
Japanese Office Action dated Oct. 26, 2020 for JP Patent Application No. 2018-528747 (4 pages, with English translation).
Chinese Office Action dated Aug. 25, 2020 for CN Patent Application No. 201680070466.6 (5 pages, with English translation).
European Search Opinion dated Jun. 30, 2016 for EP Patent Application No. 15197483.9 (23 pages).

* cited by examiner

ARYLATION METHOD

The Buchwald-Hartwig reaction can now be found in industrial manufacturing processes, in particular of intermediates for the manufacture of organic light-emitting diodes.

EP-A1-2407502 describes the preparation of dendrimers for this purpose, wherein secondary amines are obtained as intermediates through the Buchwald-Hartwig reaction. EP-A2-2421064 also uses the Buchwald-Hartwig reaction as the synthesis pathway for secondary amines that are used as intermediates.

Whilst the moderate yield is disadvantageous the lack of selectivity poses the greater problem resulting not only in secondary but also tertiary amines as by-products. These by-products can only be separated off with difficulty by means of sublimation. Furthermore, a particular disadvantage is that intermediates used in the manufacture of organic light-emitting diodes are subject to particularly high purity requirements as unwanted, even structurally related impurities, even in small quantities, can lead to an undesirable shift in the emission wavelengths or to a reduction in the quantum yield and consequently to an undesirable waste heat generation.

The object of the present patent application is to provide a method for facilitating the preparation of tri-bisphenyl amines in higher yields and selectivities under the conditions of the Buchwald-Hartwig coupling so that the cost of cleaning the compounds, which usually takes place by sublimation, can be reduced. In consideration of the above, it is necessary, therefore, to achieve the increase in yield predominantly by increasing the selectivity.

The object is accomplished by means of a method for selective arylation in accordance with the patent claims and the further description.

Short Description of the Invention

The following points provide a brief description of the invention:

1. Method for the selective arylation of a primary aromatic amine with the formula $A-NH_2$ to yield a tertiary aromatic N-ABC amine, wherein the moieties A, B and C are independently of one another the same or different substituted or unsubstituted aromatic moieties, at least one of the moieties A, B or C has a biphenyl unit, comprising the steps Reaction of the primary aromatic amine with the formula $A-NH_2$ with an aromatic compound of formula X-B, wherein X is a halogen or a trifluoromethylsulfonic acid moiety, in the presence of a first catalyst at a first reaction temperature, to obtain a secondary amine;

Reaction of the secondary amine with an aromatic compound of formula X-C, wherein X is a halogen or a trifluoromethylsulfonic acid moiety, in the presence of a second catalyst at a second reaction temperature, to obtain the tertiary aromatic amine N-ABC;

wherein the second reaction temperature is higher than the first reaction temperature, the reaction is performed in the presence of a base, and the first and the second catalyst are the same or different and each is a palladium complex, selected from the group consisting of bis-(dialkylphosphinoferrocene)palladium catalysts, catalysts with the formula $PdX_1X_2L_1L_2$, wherein $X_1$ and $X_2$ are the same or different halogen ligands, $L_1$ and $L_2$ are the same or different neutral electron donor ligands or combinations thereof.

2. Method according to point 1, wherein X1 and X2 are the same and selected from F, Cl, Br or I.
3. Method according to point 1 or 2, wherein L1 and L2 are different.
4. Method according to one or more of points 1 to 3, wherein L1 and L2 are substituted or unsubstituted neutral aromatic or heteroaromatic compounds.
5. Method according to one or more of points 1 to 4, wherein L1 is an NHC ligand.
6. Method according to one or more of points 1 to 5, wherein L2 is a pyridyl ligand.
7. Method according to one or more of points 1 to 6, wherein L1 is an NHC ligand selected from the group consisting of 1,3-bis-(2,4,6-trimethylphenyl)-imidazolidin-2-ylidene ("SIMes"), 1,3-bis-(2,6-di-isopropylphenyl)-imidazolidin-2-ylidene ("SIPr") or 1,3-bis-(2,6-di-isopropylphenyl)-imidazolin-2-ylidene (unsaturated NHC, "IPr"), bis-(2,6-di-(1-propylbutylphenyl))-4,5-dichloroimidazolin-2-ylidene and 1,3-bis-(2,6-di-(1-ethylpropylphenyl))-4,5-dichloroimidazolin-2-ylidene, and L2 is a pyridine, pyrimidine or pyrazine, which is optionally substituted once or twice with methyl, ethyl, propyl, isopropyl, tert.-butyl, chlorine, bromine or iodine, or combinations thereof,
8. Method according to one or more of points 1 to 7, wherein the alkyl substituents of the bis-(dialkylphosphinoferrocene) ligands have two to five carbon atoms.
9. Method according to one or more of points 1 to 8, wherein the aromatic carbon atoms are directly bonded to the nitrogen atom in the secondary aromatic amine, at least one of the moieties A or B has a biphenyl unit and the reaction is performed in the presence of a base and a palladium complex, wherein the palladium atom is complexed by at least one bis-(dialkylphosphinoferrocene) ligand.
10. Method according to one or more of points 1 to 9, wherein the alkyl substituents of the bis-(dialkylphosphinoferrocene) ligands have two to five carbon atoms.
11. Method according to one or more of points 1 to 10, wherein the alkyl substituents are selected from the group consisting of isopropyl, isobutyl, tert.-butyl and combinations thereof.
12. Method according to one of points 1 to 11, wherein at least two of the aromatic moieties A, B or C have a biphenyl unit which are the same or different from one another.
13. Method according to one of points 1 to 12, wherein the biphenyl unit is directly bonded to the secondary nitrogen atom of the amine.
14. Method according to one of the previous points, wherein the alkyl substituents are selected from the group consisting of isopropyl, isobutyl and combinations thereof.
15. Method according to one of the previous points, wherein the biphenyl unit is directly bonded to the leaving group, in particular a halogen, that is chlorine, bromine, iodine, or to a trifluoromethylsulfonic acid group.
16. Method according to one of the previous points, wherein the biphenyl unit is a bridged biphenyl unit of formula 2 or 3,

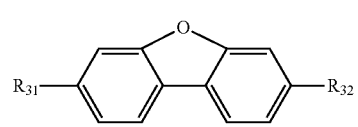

Formula 2

Formula 3

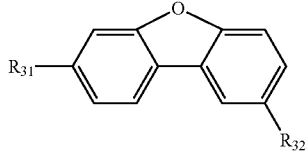

wherein D can be oxygen, sulfur, nitrogen or carbon, and in the case of nitrogen can be substituted once or in the case of carbon can be substituted twice with methyl, ethyl, biphenyl, naphthyl or phenyl, and wherein $R_{31}$ can be hydrogen, phenyl, biphenyl or pyridyl, $R_{32}$ can be a leaving group, halogen, a primary amine group NH2 or a trifluoromethylsulfonic acid moiety, depending on whether the moiety is used as A, B or C; or $R_{32}$ is a spacer which is arranged between A, B or C and X or $NH_2$.

17. Method according to one or more of the previous points, wherein at least one of the aromatic moieties A, B, C or a plurality are the same or different and selected from a unit of the formulas,

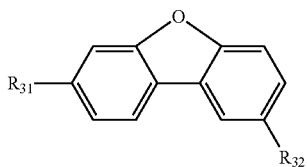

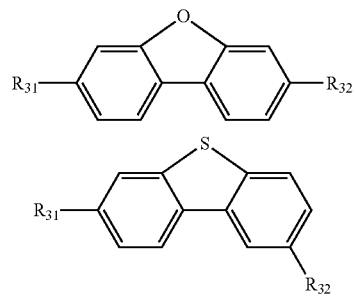

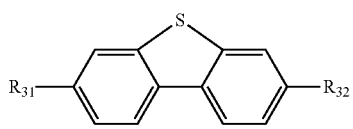

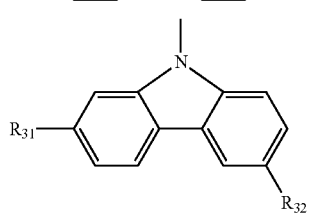

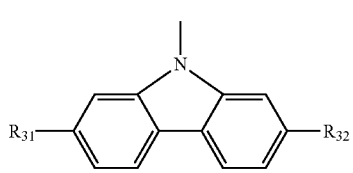

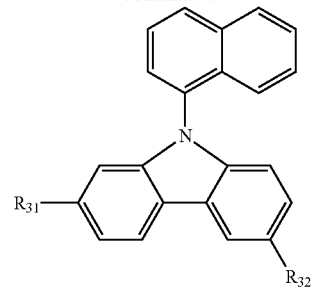

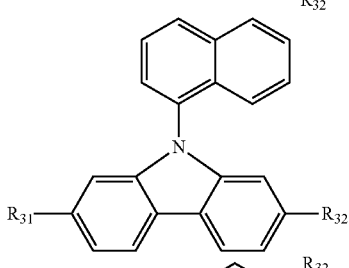

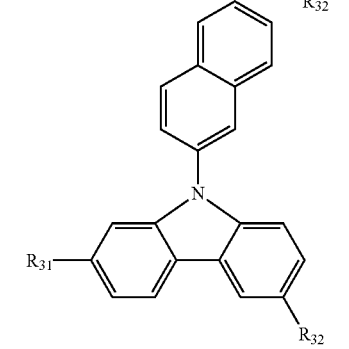

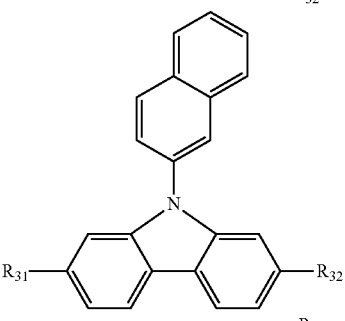

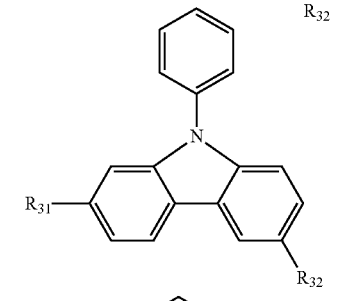

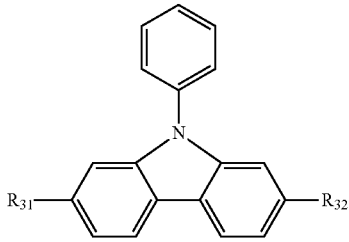

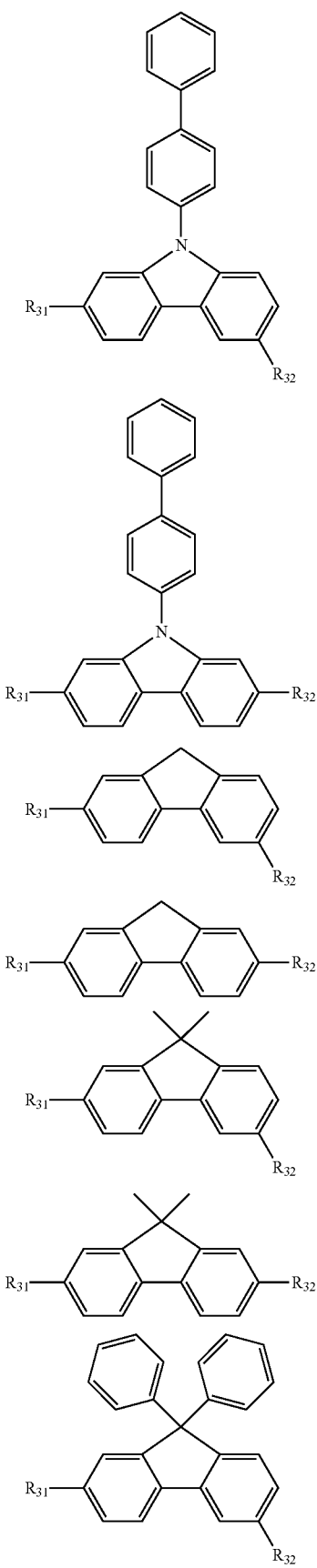

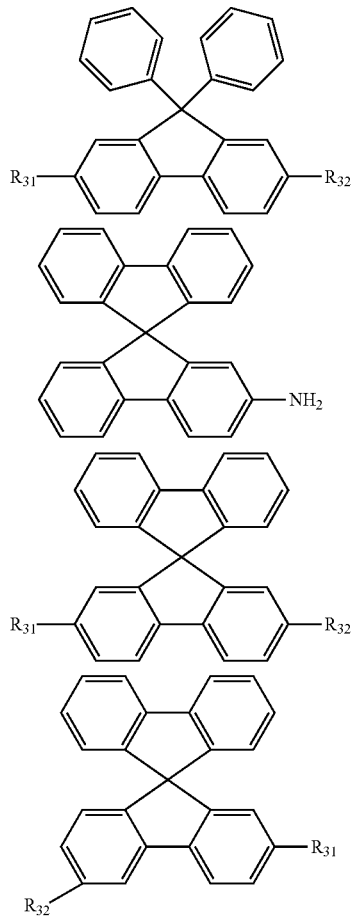

wherein R31 can be hydrogen, phenyl, biphenyl or pyridyl, R32 can be a leaving group, halogen, a primary amine group NH₂ or a trifluoromethylsulfonic acid moiety, depending upon whether the moiety is used as A, B or C; or R32 is a spacer which is arranged between A or B or C and X or NH₂.

18. Method according to one or more of the previous points, wherein the spacer is selected from the group consisting of 1,4-phenyl, 1,4-(6-methyl)phenyl, 1,4-(5-methyl)phenyl, 4,4'-biphenyl, 2,6-naphthyl, 1,4-naphthyl,

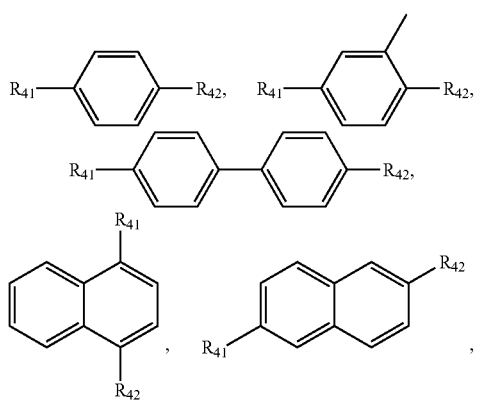

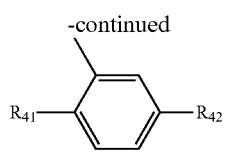

and wherein R41 here is a structure of formulas 2 to 22, R42 is a halogen such as fluorine, chlorine, bromine, iodine or astatine, a primary amine group NH₂ or a trifluoromethylsulfonic acid moiety.

19. Method according to one or more of the previous points, wherein the base is lithium hydroxide, potassium hydroxide, sodium hydroxide, tertiary organic amines, alkoxides, tributylamine, triethylamine, alkaline metal alkoxides, lithium ethanolate, sodium ethanolate, potassium ethanolate, lithium tert. butanolate, sodium tert. butanolate, potassium tert. butanolate, lithium bis(trimethylsilyl)amide, sodium bis(trimethylsilyl)amide, potassium bis(trimethylsilyl)amide, sodium or potassium salts of BHT (2,6-di-tert.-butylhydroxytoluol), or combinations thereof.

20. Method according to one or more of the previous points, wherein the method is performed in a solvent selected from the group consisting of alcohols, ethanol, propanol, isopropanol, butanol, isobutanol, ethylene glycol, ether, diethyl ether, tert.-butylethyl ether, tert.-butylmethyl ether, tetrahydrofuran, dioxane ethylene glycol dimethyl ether, bis(2-methoxyethyl)ether, aromatic solvents, benzene, toluene, xylene, o-xylene, p-xylene, m-xylene and combinations thereof.

21. Method according to one or more of the previous points, wherein the first temperature is 5° C. to 95° C., 30° C. to 90° C., 50° C. to 80° C. or 55° C. to 70° C., the second temperature is from 90° C. to 144° C., 100° C. to 139° C., 111'C to 138° C. or 115° C. to 125° C.

22. Method according to one or more of the previous points, wherein the reaction time of the method step to prepare the secondary amine and the method step to prepare the tertiary amine is respectively from one hour to 36 hours, 4 hours to 24 hours, 6 hours to 16 hours, or 8 hours to 12 hours.

23. Method according to one or more of the previous points, wherein the biphenyl unit is 2-fluorene, 3-fluorene, 2-(9,9-diphenylfluorene), 2-(9,9-dimethylfluorene), 3-(9,9-diphenylfluorene), 3-(9,9-dimethylfluorene), 3-(4-phenyl)-9-phenyl-9H-carbazole, 3-(4-phenyl)-9-methyl-9H-carbazole, 3-(4-phenyl)-9-biphenyl-9H-carbazole, 2-(4-phenyl)-9-phenyl-9H-carbazole, 2-(4-phenyl)-9-methyl-9H-carbazole, 2-(4-phenyl)-9-biphenyl-9H-carbazole, 3-(4-biphenyl)-9-phenyl-9H-carbazole, 3-(4-biphenyl)-9-methyl-9H-carbazole, 3-(4-biphenyl)-9-biphenyl-9H-carbazole, 2-(4-biphenyl)-9-phenyl-9H-carbazole, 2-(4-biphenyl)-9-methyl-9H-carbazole, 2-(4-biphenyl)-9-biphenyl-9H-carbazole, 3-(9-phenyl-9H-carbazole), 3-(9-methyl-9H-carbazole), 3-(9-biphenyl-9H-carbazole), 2-(9-phenyl-9H-carbazole), 2-(9-methyl-9H-carbazole), 2-(9-biphenyl-9H-carbazole) or triphenylene.

24. Method according to one or more of the previous points, wherein the palladium complex is used in quantities of 0.01 mol % to 1.5 mol %, in relation to the total molar quantity of both educts, the aromatic amine A-NH₂ or AB-NH and the aryl halides X-B or X-C.

25. Method according to one or more of the previous points, wherein the palladium complex is used as a solid, solution or powder mixture with a solid bis-(dialkylphosphinoferrocene).

26. Method according to one of the previous points, comprising the steps:
    Providing the primary aromatic amine A-NH₂, the aryl halide X-B, a suitable solvent and, where applicable, a bis-(dialkylphosphinoferrocene) in a reaction vessel;
    Adding a palladium complex, in which the palladium atom is complexed by at least one bis-(dialkylphosphinoferrocene) ligand, in the form of a solid or a solution;
    Heating the reaction mixture thus obtained in the reaction vessel;
    Separating off the reaction product, a secondary aromatic amine A-NH-B; and,
    where applicable cleaning the secondary aromatic amine A-NH-B.

27. Method according to one of the previous points, comprising the steps;
    Providing the primary aromatic amine A-NH₂, the aryl halide X-B, a suitable solvent and, where applicable, a bis-(dialkylphosphinoferrocene) in a reaction vessel;
    Adding a palladium complex, in which the palladium atom is complexed by at least one bis-(dialkylphosphinoferrocene) ligand, in the form of a solid or a solution;
    Heating the reaction mixture thus obtained to the first reaction temperature;
    Adding an aryl halide X-C;
    Heating to the second reaction temperature; and
    Separating off and, where applicable, cleaning the tertiary aromatic amine N-ABC.

28. Method according to one or more of the previous points, wherein the compounds

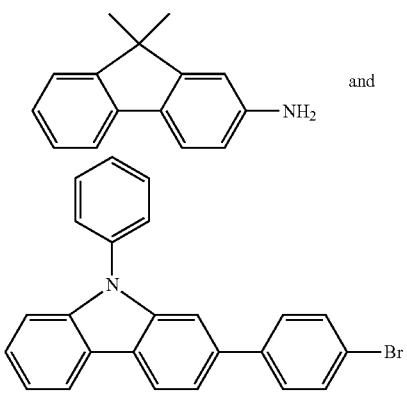

are available.

29. Method according to one or more of the previous points, wherein the palladium atom in the palladium complex is additionally complexed by 2,4,6,8-tetramethylcyclotetrasiloxane, bis(dibenzylideneacetone) or maleimide.

30. Method according to one or more of the previous points, wherein the palladium atom in the palladium complex is complexed by 1,1-bis(diisopropylphosphino)ferrocene.

31. Method according to one or more of the previous points, wherein the aromatic carbon atoms are directly bonded to the nitrogen atom in the secondary aromatic amine.

DETAILED DESCRIPTION OF THE INVENTION

The first catalyst and the second catalyst are both palladium complexes. They may be the same or different.

In the palladium complex, the palladium atom may be complexed by at least one bis-(dialkylphosphinoferrocene) ligand, which has the general formula 1:

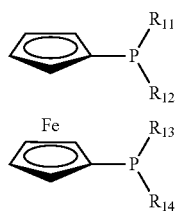

Formula 1

In this case, they are referred to as a bis-(dialkylphosphinoferrocene)palladium complex or bis-(dialkylphosphinoferrocene)palladium catalyst.

With these complexes, R11 to R14 may be the same or different and are, in particular, alkyl moieties with one to five carbon atoms. R11 to R14 can, therefore, be selected independently of each other from methyl, ethyl, n-propyl, isopropyl, n-butyl, isobutyl, sec.-butyl, tert.-butyl, n-pentyl (amyl), 2-pentyl (sec-pentyl), 3-pentyl, 2-methylbutyl, 3-methylbutyl (iso-pentyl or iso-amyl), 3-methylbut-2-yl, 2-methylbut-2-yl,2,2-dimethylpropyl (neopentyl).

Advantageously, R11 to R14 are the same and selected from the group consisting of methyl, ethyl, n-propyl, isopropyl, n-butyl, isobutyl, sec.-butyl, tert.-butyl, n-pentyl (amyl), 2-pentyl (sec-pentyl), 3-pentyl, 2-methylbutyl, 3-methylbutyl (iso-pentyl or iso-amyl), 3-methylbut-2-yl, 2-methylbut-2-yl,2,2-dimethylpropyl (neopentyl).

Isopropyl, isobutyl, tert.-butyl, in particular isopropyl and tert.-butyl, are particularly suitable. Good results are achieved if R11 to R14 are the same and are isopropyl or tert.-butyl. Good results are achieved in particular if RI 1 to R14 are the same and are isopropyl, propyl or isobutyl. Good results are achieved in particular if R11 to R14 are the same and are isopropyl.

The palladium complex, which may be used as the first or second catalyst, may also be a palladium complex with the general formula $PdX_1X_2L_1L_2$, wherein $X_1$ and $X_2$ are the same or different halogen ligands, $L_1$ and $L_2$ are the same or different neutral electron donor ligands. In general, fluorine, chlorine, bromine or iodine, in particular chlorine or bromine, may be used as halogen ligands $X_1$ and $X_2$.

Phosphines, such as tri-iso-propylphosphine, tricyclohexylphosphine ($PCy_3$) or tricyclopentylphosphine, triphenylphosphine, tri-ortho-tolylphosphine, for example, may be used as neutral electron donor ligands. Phospha-bicycloalkanes, such as 9-phosphabicyclo-[3.3.1]-nonane or 9-phosphabicyclo-[4.2.1]-nonane (also known as "phobane"), may also be suitable, also suitable are 9-cyclohexyl-9-phospha-bicyclo-[3.3.1]-nonane ("cyclohexylphobane"), 9-(2,2,4-trimethylpentyl)-9-phospha-bicyclo-[3.3.1]-nonane ("2,2,4-trimethylpentyl phobane") and 9-isobutyl-9-phospha-bicyclo-[3.3.1]-nonane ("isobutylphobane").

N-heterocyclic carbene ligands, which are also referred to as "NHC ligands", are also suitable.

Well suited here are stable nitrogenous heterocyclic compounds that contain at least one nitrogen atom and have several carbon atoms as ring atoms. At least one of the nitrogen atoms in the ring is bonded with an organic moiety that is not part of the heterocyclic ring structure. Particularly suitable are NHC ligands of formulas (III) and (IV), in particular of formula (IV).

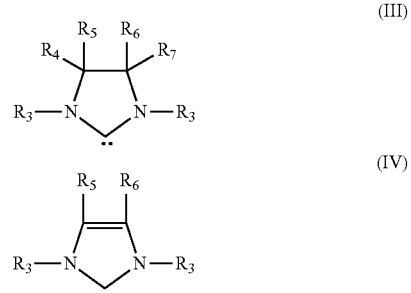

In formulas (III) and (IV), $R_3$ is a substituted aryl group selected from the group consisting of 2,4,6-trimethylphenyl ("mesityl"), 2,6-di-isopropylphenyl, 2,6-di-(1-ethylpropyl) phenyl, 2,6-di-(1-propylbutyl)phenyl, 3,5-di-tert.-butylphenyl and 2-methylphenyl, and combinations thereof. Well suited is 2,6-di-(1-ethylpropylphenyl), which can also be perceived as 2,6-di-(3-pentyl)phenyl, or 2,6-di-(1-propyl-butyl)phenyl, which can also be perceived as 2,6-di-(4-heptyl)phenyl.

In formulas (Ill) and (IV), $R_5$ and $R_6$ are selected independently of one another from hydrogen, halogen, methyl, nitro groups, or $R_5$ and $R_6$ form a ring with a total of 4 to 8, in particular 5 to 6, carbon atoms. In particular, $R_5$ and $R_6$ are selected independently of one another from hydrogen, chlorine, bromine, iodine, or combinations thereof. In one specific embodiment, $R_5$ and $R_6$ are the same.

In formulas (III) and (IV), $R_4$ and R7 are selected independently of one another from hydrogen, halogen, methyl, nitro groups and combinations thereof. In particular, $R_4$ and $R_7$ are the same and selected from hydrogen, chlorine, bromine, or iodine. In particular, $R_4$ and $R_7$ are hydrogen.

The NHC ligand is in particular selected from the group consisting of 1,3-bis-(2,4,6-trimethylphenyl)-imidazolidin-2-ylidene ("SIMes"), 1,3-bis-(2,6-di-isopropylphenyl)-imidazolidin-2-ylidene ("SIPr") or 1,3-bis-(2,6-di-isopropylphenyl)-imidazolin-2-ylidene (unsaturated NHC, "IPr"), bis-(2,6-di-(1-propyl butyl phenyl))-4,5-dichloroimidazolin-2-ylidene or 1,3-bis-(2,6-di-(1-ethylpropylphenyl))-4,5-dichloroimidazolin-2-ylidene.

The NHC ligand is particularly suitable as $L_1$.

Pyridyl ligands are also suitable as electron donor ligands. They are pyridine, pyrimidine, pyrazine and their derivatives, that is substituted pyridine, pyrimidine or pyrazine. The complexing of the palladium atom takes place via the heterocyclic nitrogen atom.

Pyridine, pyrimidine or pyrazine can be substituted once or twice with alkyl, nitro, halogen, in particular methyl, ethyl, propyl, isopropyl, tort-butyl, chlorine, bromine or iodine. In a special embodiment, pyridine, pyrimidine or pyrazine is substituted once with methyl, ethyl, propyl, isopropyl, tert.-butyl, nitro, chlorine, bromine or iodine, Alkyl substituents here are, in particular, in 2- or 6- ("ortho") or 4- ("para") position to the complexing nitrogen atom, that is to the nitrogen atom that coordinates the palladium. Nitro groups or halogen atoms (fluorine, chlorine, bromine, iodine) are in particular arranged in 3-position ("meta" position) to the complexing nitrogen atom.

Therefore, pyridine, pyrimidine, pyrazine, 3-chloropyridine, 4-methylpyridine, 2-methylpyridine, 2,6-dimethylpyridine, 5-chloropyrimidine, 4-methylpyrimidine, chloropyrazine are particularly suitable.

Pyridine, pyrimidine, pyrazine and their derivatives are, in particular, well suited as $L_2$.

In a specific embodiment, the halogen ligands $X_1$ and $X_2$ in the palladium complex $PdX_1X_2L_1L_2$ are the same and chlorine or bromine, $L_1$ and $L_2$ are different from one another, wherein $L_1$ is an NHC ligand and $L_2$ is a pyridine, pyrimidine, pyrazine or one of their derivatives.

In particular, the halogen ligands $X_1$ and $X_2$ are the same and chlorine, $L_1$ is an NHC ligand in particular selected from the group consisting of 1,3-bis-(2,4,6-trimethylphenyl)-imidazolidin-2-ylidene ("SIMes"), 1,3-bis-(2,6-di-isopropylphenyl)-imidazolidin-2-ylidene ("SIPr") or 1,3-bis-(2,6-di-isopropylphenyl)-imidazolin-2-ylidene (unsaturated NHC, "IPr"), or 1,3-bis-(2,6-di-(1-ethylpropylphenyl))-4,5-dichloroimidazolin-2-ylidene, bis-(2,6-di-(1-propylbutylphenyl))-4,5-dichloroimidazolin-2-ylidene, and $L_2$ is selected from the group consisting of pyridine, pyrimidine, pyrazine, 3-chloropyridine, 4-methylpyridine, 2-methylpyridine, 2,6-dimethylpyridine, 5-chloropyrimidine, 4-methylpyrimidine, 3-chloropyrazine.

Specific suitable compounds are the compounds commercially available as Pd-PEPPSI$^{pyr}$-IPR, Pd-PEPPSI$^{2,6\text{-}di\text{-}Me}$-IPR, Pd-PEPPSI$^{2Me}$-IPR, Pd-PEPPSI$^{pyr}$-IPR, Pd-PEPPSI$^{2,6\text{-}di\text{-}Me}$-IPR$^{Cl}$, Pd-PEPPSI$^{pyr}$-IPent, Pd-PEPPSI$^{2Me}$-IPent, Pd-PEPPSI-IPR$^{Me}$, Pd-PEPPSI-IPR$^{Cl}$, Pd-PEPPSI-IPR$^{Qino}$, Pd-PEPPSI-IHEPT, Pd-PEPPSI-IHEPT$^{Cl}$ with the following formulas.

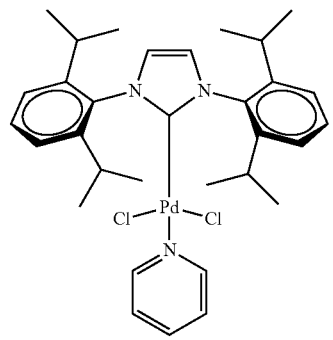

Pd-PEPPSI$^{pyr}$-IPr

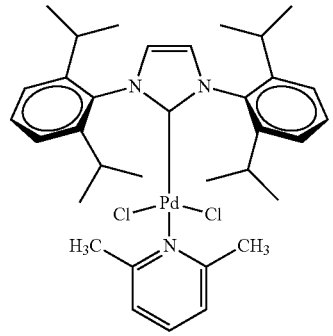

Pd-PEPPSI$^{2,6\text{-}DiMe}$-IPr

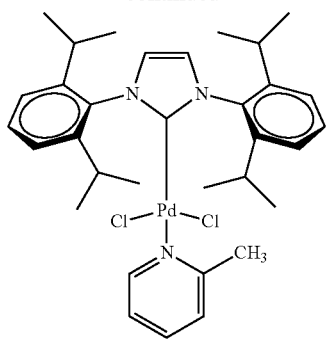

Pd-PEPPSI$^{2Me}$-IPr

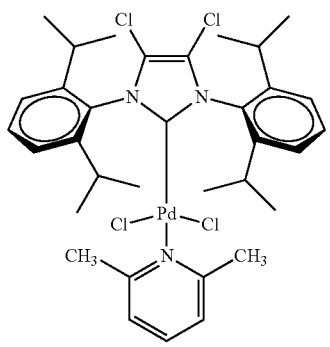

Pd-PEPPSI$^{2,6\text{-}DiMe}$-IPr$^{Cl}$

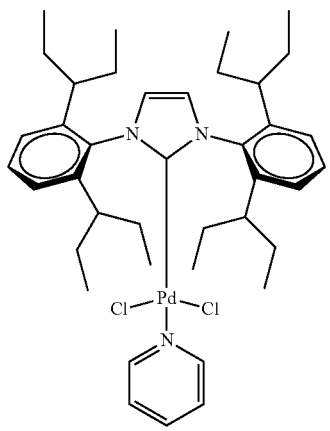

Pd-PEPPSI$^{pyr}$-IPent

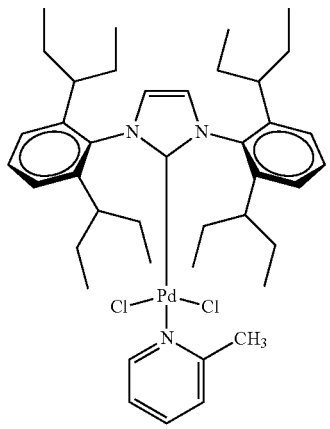

Pd-PEPPSI$^{2Me}$-IPent

-continued

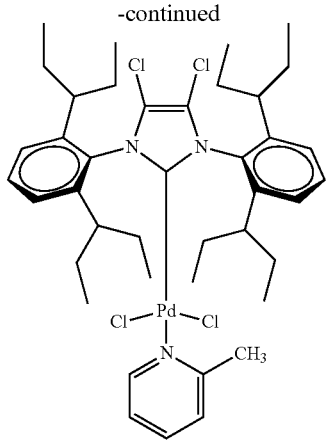

Pd-PEPPSI²ᴹᵉ-IPent^Cl

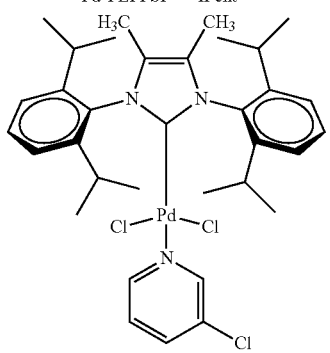

Pd-PEPPSI-IPr^Me

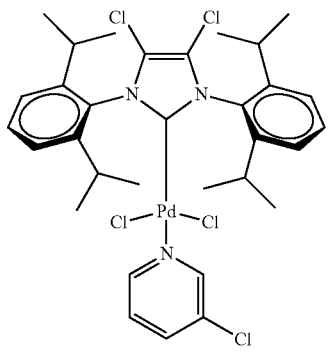

Pd-PEPPSI-IPr^Cl

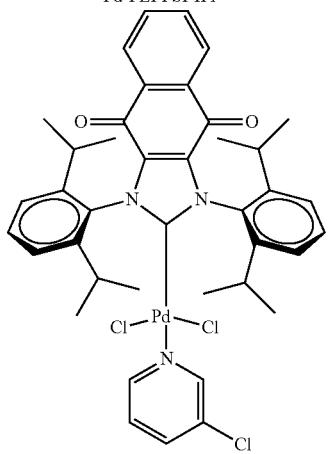

Pd-PEPPSI-IPr^Cino

-continued

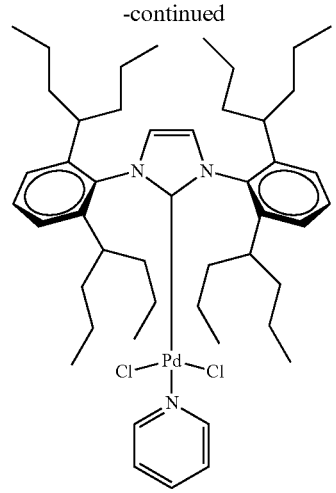

Pd-PEPPSI-IHept

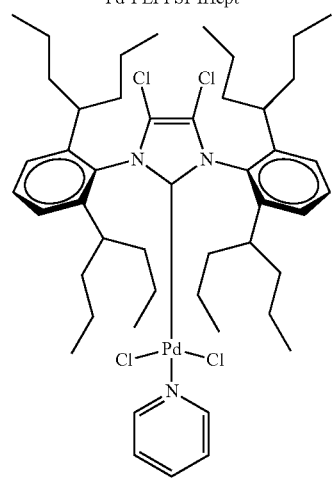

Pd-PEPPSI-IHept^Cl

In particular, a palladium complex $PdX_1X_2L_1L_2$, in which the halogen ligands $X_1$ and $X_2$ are chlorine, $L_1$ is bis-(2,6-di-(1-ethylpropylphenyl))-4,5-dichloroimidazolin-2-ylidene and $L_2$ is 3-chloropyridine, is well suited. This complex has the structure of formula (V) and is commercially available, for example, under the name Pd-PEPPSI-IPent^Cl (Total Synthesis Ltd.).

Formula (V)

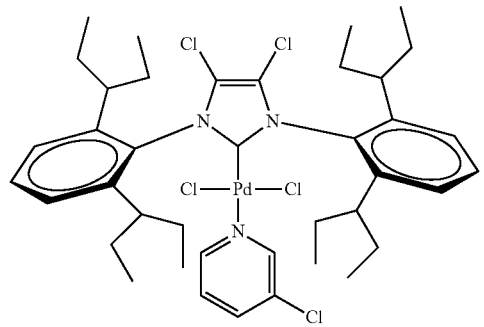

Surprisingly, it was found that palladium complexes of the bis(dialkylphosphinoferrocene) ligand of formula 1 not only allow the selective production of the secondary amines with high yields during the preparation of secondary amines through Buchwald-Hartwig coupling if at least one of the moieties A or B of the compounds to be coupled have at least one biphenyl unit as a structural element but are also well suited at higher temperatures for a further reaction to yield the tertiary amine by reacting the secondary amine thus obtained with a compound of the type X-C.

The same applies to palladium complexes with the general formula $PdX_1X_2L_1L_2$, which are also described above.

The amount of palladium used here can be reduced from the 3 mol % normally used to approx. 1.5 mol % or less, wherein the double arylation to yield the tertiary amine normally occurring as a side reaction is suppressed and the reaction to yield the desired product takes place with conversions usually of 90% or more. Surprisingly, the same was observed for palladium complexes with the general formula $PdX_1X_2L_1L_2$, which are described above, in particular for the palladium catalysts sold by Total Synthesis Ltd. under the name "Pd-PEPPSI."

Preferably, at least two of the moieties A, B and C have one biphenyl unit. The biphenyl unit can be unsubstituted or substituted, also with one or a plurality of phenyl moieties, so that for example terphenyl-, quaterphenyl- or triphenylene units form, which can be substituted or unsubstituted. The biphenyl units can also be bridged, as for example in the case of fluorene and its derivatives.

As biphenyl, the compounds of formulas 2 or 3 in particular can be used as moieties A or B:

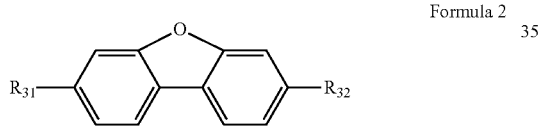

Formula 2

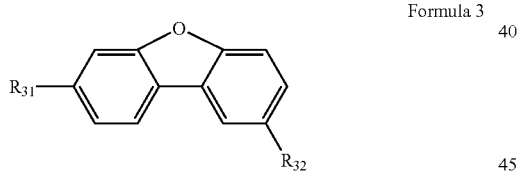

Formula 3

D can be oxygen, sulfur, nitrogen or carbon and may be substituted once (in the case of nitrogen) or twice (in the case of carbon) with methyl, ethyl, biphenyl, 1-naphthyl, 2-naphthyl or phenyl. Therefore, the following moieties can in particular be present:

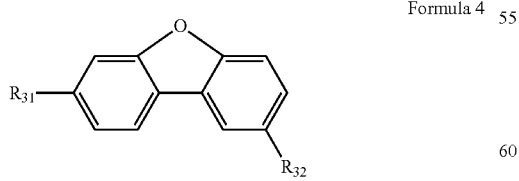

Formula 4

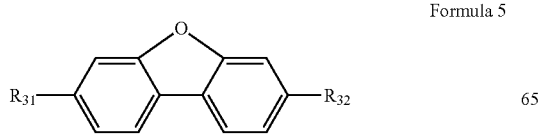

Formula 5

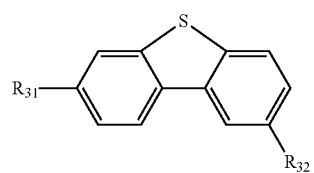

Formula 6

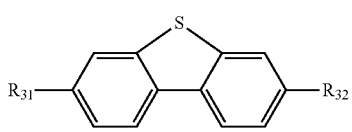

Formula 7

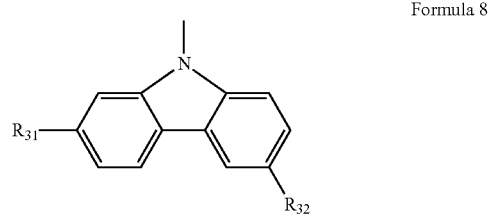

Formula 8

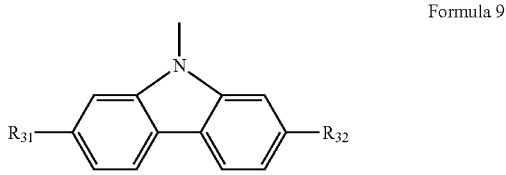

Formula 9

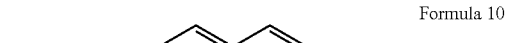

Formula 10

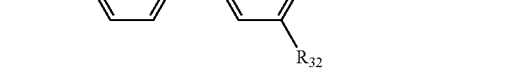

Formula 11

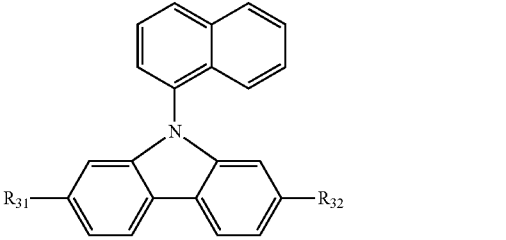

Formula 12

Formula 13
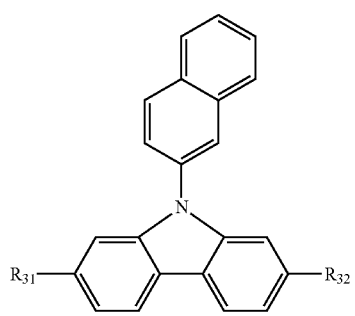
Formula 14
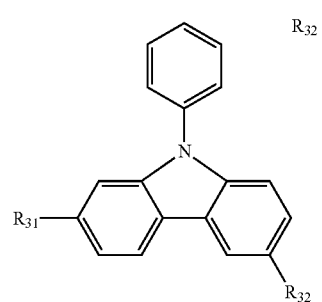
Formula 15
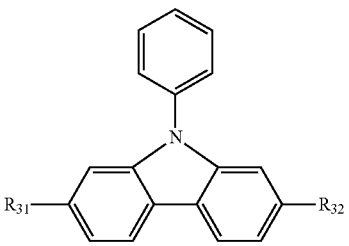
Formula 14
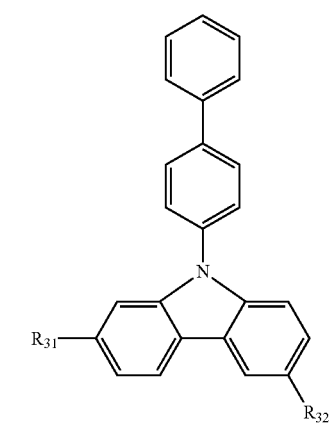
Formula 15
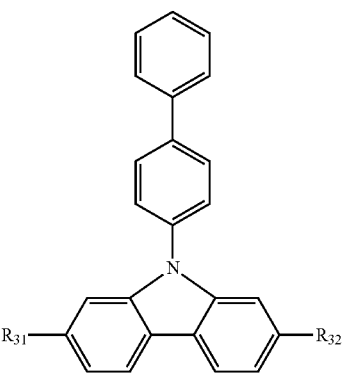
Formula 16
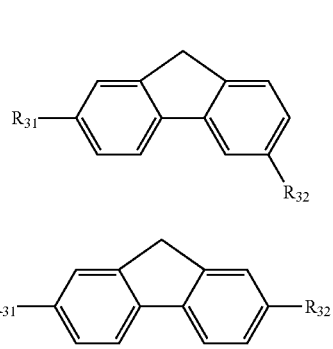
Formula 17
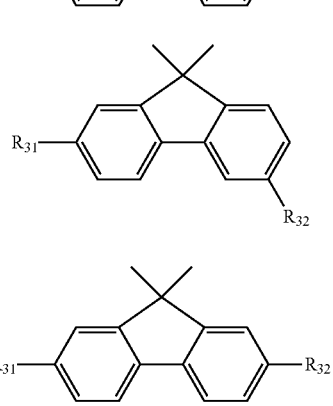
Formula 18
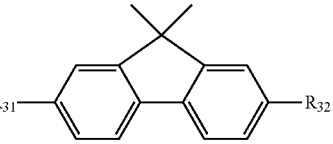
Formula 19
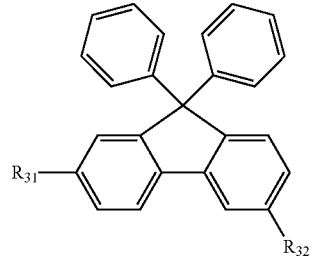
Formula 20
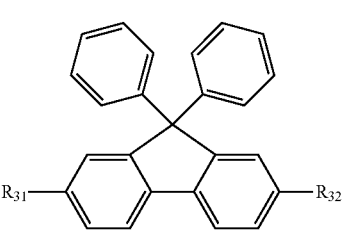
Formula 21

-continued

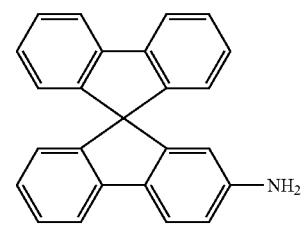

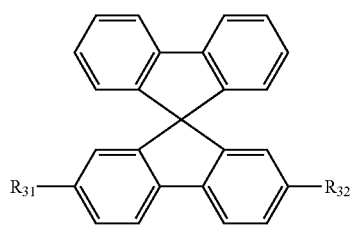

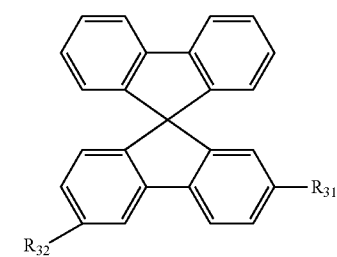

R31 can be hydrogen, phenyl, biphenyl or pyridyl.

R32 can either be, as described above, halogen, a primary amine group NH$_2$ or a trifluoromethylsulfonic acid moiety, depending on whether the moiety of formula 2 or 3 is used as A or B.

However, R32 can also be a spacer which is arranged between A or B and X or NH$_2$. Suitable spacers are, for example, 1,4-phenyl, 1,4-(6-methyl)phenyl, 1,4-(5-methyl)phenyl, 4,4'-biphenyl, 2,6-naphthyl or 1,4-naphthyl. They are in particular Formula 32

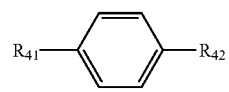

Formula 33

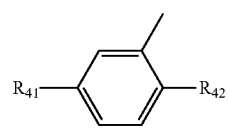

Formula 34

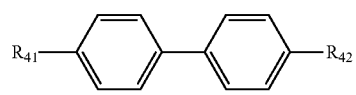

Formula 35

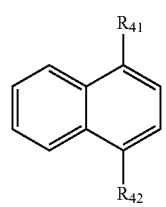

-continued

Formula 36

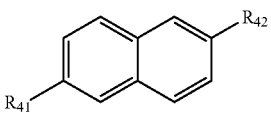

Formula 37

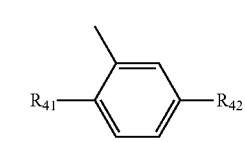

R41 here is a structure of formulas 2 to 22, R42 can be a halogen, such as fluorine, chlorine, bromine, iodine or astatine, a primary amine group NH$_2$ or a trifluoromethyl-sulfonic acid moiety.

In a specific embodiment of the invention, the following compounds are used, the compound of formula 131 as amine of formula A-NH$_2$ and the compound of formula 132 as aryl halide of formula B-X Formula 131

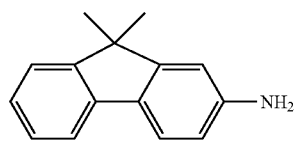

Formula 132

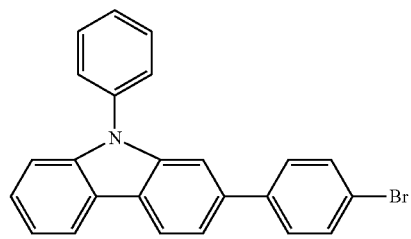

Formula 133

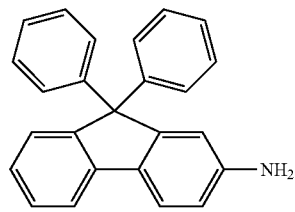

The starting compounds, the primary aromatic amine A-NH$_2$ and the aryl halide X-B, are used in an equimolar manner. Where applicable, the aryl halide or the amine can also be used in an excess up to 1.1 times or 1.2 times the equimolar ratio.

A further reaction of the secondary amine with a further aryl halide X-C is required to prepare the tertiary amine N-ABC, which is expressed more precisely by the following structural formula

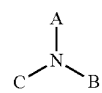

X-C like X-B is defined above and can be identical to X-B or different from it. In particular C is 4-biphenyl, 3-biphenyl or 2-fluorobiphenyl-4-yl, 2-naphthyl, carbazole-9-yl, quinoline-6-yl, 2-phenylquinazoline-4-yl.

C can, in particular, also have the following structures,

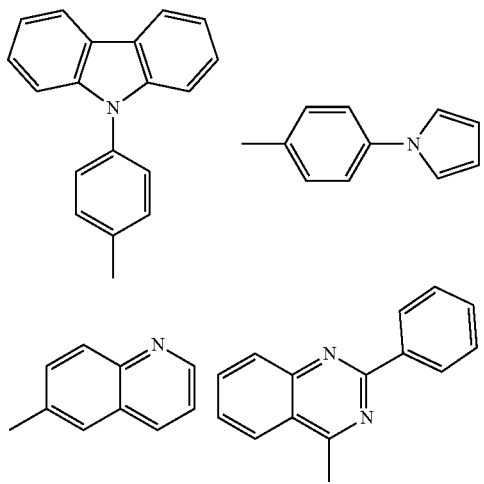

The palladium complexes can be obtained in a manner known in principle. To this end, a palladium compound is first presented in a solvent and then the desired bis-(dialkylphosphinoferrocene) ligand is added, wherein good results can be achieved with 1,1'-bis(diisopropylphosphino) ferrocene, 1,1'-bis(diisobutylphosphino)ferrocene, 1,1'-bis (di-tert.-butylphosphino)ferrocene. It can then be stirred for between 30 and 1000 minutes, in particular 40 to 400 minutes or 50 to 120 minutes. The reaction temperature can be from approx. 10° C. to 100° C., in particular 15° C. to 50° C. or 20° C. to 30° C.

Good results can already be achieved by stirring at room temperature for around one hour.

The upper limit for the temperature largely depends on the boiling temperature of the solvent so that high-boiling solvents are required for higher reaction temperatures and the upper temperature limits given above can be seen not as rigid but as being dependent upon the boiling temperature of the solvent.

In general, suitable solvents are aprotic solvents, such as ether or aromatic solvents. Therefore, for example, diethyl ether, tert.-butylethyl ether, tert.-butylmethyl ether, tetrahydrofuran or dioxane are suitable, but benzene, toluene or xylene, as well as acetonitrile can also be used.

Good results can be achieved by using preferably water-free and oxygen-free solvents, which can be obtained through conventional drying processes for the solvents.

Palladium compounds suitable as educt for the palladium complex can be Pd (0) and Pd(II) complexes, such as allylchloro[1,3-bis(2,4,6-trimethylphenyl)imidazol-2-ylidene]palladium(II), (ethylenediamine)palladium(II) chloride, palladium(II) acetate, palladium(II) chloride, palladium pivalate, palladium(II) acetylacetonate, bis(benzonitrile)palladium(II) chloride, bis(acetonitrile)dichloropalladium(II), diamminedichloropalladium(II), dichloro(1,5-cyclooctadiene)palladium(II), palladium(II) nitrate, palladium(II) oxide, palladium(II) oxide hydrate, $H_2[PdCl_4]$, diamminedinitritopalladium(II), palladium(II) sulfate, tetraamminepalladium(II) sulfate $[Pd(NH_3)_4]SO_4$, tetraamminepalladium(II) hydrogen carbonate, tetraamminepalladium(II) chloride $[Pd(NH_3)_4]Cl_2$, potassium tetrachloropalladate(II) $K_2[PdCl_4]$, sodium tetrachloropalladate (II) $Na_2[PdCl_4]$, ammonium tetrachloropalladate(II) $(NH_4)_2[PdCl_4]$, tetraamminepalladium(II) nitrate, 1,3-divinyl-1,1,3,3-tetramethyldisiloxanepalladium(0) (also as Pd-VTS, Pd-VS or palladium-VTS), bis(dibenzylideneacetone) palladium(0) $(Pd(dba)_2)$, $(Pd_2(dba)_3)$. $(Pd_2(dba)_3)$-LM, wherein LM is a solvent, in particular $CHCl_3$ or $CH_2Cl_2$. In this way, a catalyst solution can be obtained.

The palladium complexes of the type $PdX_1X_2L_1L_2$ are commercially available, for example from Total Synthesis Ltd, and can be produced in a way such as that described in Angewandte Chemie [Applied Chemistry], International Edition 2012, 51(45), 11354-11357 as well as in Angewandte Chemie, International Edition 2014, 53(12), 3223-3226, as well as the supplementary information in this respect. The synthesis can occur, for example, by reacting the imidazole derivative, which is used as $L_1$, at room temperature under inert gas and with the exclusion of water and oxygen in an ether, for example tetrahydrofuran (THF), with a base, such as alkaline metal alkoxide, for example potassium-tert.-butanolate, at room temperature. The reaction time is generally 1 to 4 hours, approx. 2 hours are often sufficient. The base is advantageously used slightly hyperstoichiometrically, that is in quantities of approx. 1.05 to 1.2 equivalents, in particular approx. 1.1 equivalents. Approximately half the molar quantity $[(\eta^3\text{-allyl})Pd(\mu\text{-Cl})]_2$ is then added as this compound is a dimer. This reaction is also performed at room temperature under inert gas, and with the exclusion of water and oxygen. The reaction time is approx. 20 to 24 hours. After the precipitate has been filtered and washed, it is reacted for 1 to 4 days, usually 2 days, at room temperature in ethereal hydrochloric acid, that is a solution of hydrogen chloride gas in diethyl ether, wherein 2 molar ethereal hydrochloric acid has proven effective. In this way, the second halogen ligand is introduced to the palladium atom. After the solvent has been removed, for example by means of distillation, in a further step using a suitable solvent, such as haloalkanes, chloroform, dichloromethane or tetrachloroethane for example, is reabsorbed and the desired ligand $L_2$ is added to the solution obtained. Suitable ligands are described above, advantageously nitrogen heterocyclic compounds, in particular pyridine, pyrimidine or pyrazine, as well as their derivatives, are used, pyridine or 3-chloropyridine in particular have proven effective here. This reaction is carried out for up to four hours at room temperature. The final steps are also performed under inert gas, that is with the exclusion of water and oxygen. The solvent can be removed after the reaction and the product cleaned further using column chromatographic methods.

After the palladium complex has been produced, the process can be continued by adding the other reactants, that is the primary aromatic amine $A-NH_2$, the aryl halide X-B and the base required for the Buchwald-Hartwig coupling, to the catalyst solution within the meaning of a one pot synthesis. Alkali and alkaline earth metal hydroxides, such as lithium hydroxide, potassium hydroxide or sodium hydroxide, are suitable as a base. Tertiary organic amines or alkoxides, such as tributylamine, triethylamine, alkali metal alkoxides, such as lithium ethanolate, sodium ethanolate or potassium ethanolate, lithium-tert.-butanolate, sodium-tert.-butanolate or potassium-tert.-butanolate, lithium bis(trimethylsilyl)amide, sodium bis(trimethylsilyl)amide, potassium bis(trimethylsilyl)amide, individually or in combination with one another, are also suitable as a base. Alkali metal salts of BHT (2,6-di-tert.-butylhydroxytoluol), in particular the sodium or potassium salt, have proven effective, good results can be achieved hereby particularly with the use of palladium complexes of type PdX1X2L1 L2, in particular with the use of this complex as first catalyst.

In relation to the overall molar quantity of the educts, of the primary aromatic amine A-NH$_2$ and of the aryl halide X-B or of the secondary amine AB-NH and of the aryl halide X-C, the base can generally be used in quantities of 40% to 80%, in particular 50% to 70% or 55% to 65%, This means that if, for example, 20 mmol respectively of the primary aromatic amine A-NH$_2$ and of the aryl halide X-B, therefore 40 mmol in total, are used, the base can be used in quantities of 16 mmol to 32 mmol, in particular 20 mmol to 28 mmol or from 22 mmol to 26 mmol. The same applies when using the secondary amine AB-NH and the aryl halide X-C.

As an alternative to this procedure, the primary aromatic amine A-NH$_2$, the aryl halide X-B and the base provided with a solvent can also be introduced and the catalyst solution can be added in the appropriate quantity.

The conventional solvents for Buchwald-Hartwig couplings, that is alcohols, such as ethanol, propanol, isopropanol, butanol, isobutanol but also for example ethylene glycol, ether, such as diethyl ether, tert.-butylethyl ether, tert.-butylmethyl ether, tetrahydrofuran, dioxane ethylene glycol dimethyl ether, bis(2-methoxyethyl)ether, aromatic solvents, such as benzene, toluene, or xylenes, such as o-xylol, p-xylol, m-xylol, as well as mixtures thereof, or combinations of these solvents, are suitable as solvents for the coupling reaction between the aromatic amine A-NH$_2$ and the aryl halide X-B or the secondary amine AB-NH and the aryl halide X-C. As for the solvents, it should be ensured that they are inert under the conditions of the Buchwald-Hartwig coupling as amino or halogen groups can interfere with the desired reaction.

The quantity of catalyst required for the reaction is between 0.01% to 1.5 mol %, or from 0.1 to 1 mol %, or from 0.2 mol % to 0.8 mol %. The specification in mol % refers to the total quantity in mol of the educts of the respective stage, of the primary aromatic amine A-NH$_2$ and of the aryl halide X-B or of the secondary aromatic amine AB-NH and of the aryl halide X-C. The secondary aromatic amine AB-NH, which inevitably occurs as an intermediate, can be isolated and cleaned before the reaction to yield tertiary amine ABC-N. However, the reaction can also be carried out as a one-pot synthesis, by introducing the base, the primary aromatic amine A-NH$_2$ and the aryl halide X-B in a solvent and reacting them in the presence of a catalyst. The aryl halide X-C can then be added and the reaction continued at the second reaction temperature. In so doing, the second catalyst can also be added to the secondary amine following the reaction. The first and the second catalyst are preferably the same in this case. Particularly advantageously in this case, a sufficient quantity of the catalyst is available right at the beginning for the reaction of the primary aromatic amine A-NH$_2$ and the aryl halide X-B so that the reaction to yield the tertiary amine can be effected without the addition of additional catalyst but rather by simply adding the aryl halide X-C and changing the temperature to the second reaction temperature.

The conversions of the educts are at least at 90%, in particular at at least 95% or at least 97%.

The first reaction temperature is generally 5° C. to 95° C., in particular 30° C. to 90° C., 50° C. to 80° C. or 55° C. to 70° C.

The second reaction temperature is higher than the first respectively used reaction temperature and is generally approx. 90° C. to approx. 144° C., in particular 111° C. to 130° C. or 100° C. to 139° C. or 115° C. to 125° C. or 100° C. to 111° C.

The reaction times for both the reaction step to yield the secondary amine and the further reaction to yield the tertiary amine can be respectively one hour to 36 hours, or 4 hours to 24 hours, or 6 hours to 16 hours, or 8 hours to 12 hours.

In an advantageous embodiment, the corresponding ligand, that is the bis-(dialkylphosphinoferrocene) ligand used in the palladium complex, is also added as catalyst along with the palladium complex, wherein the palladium atom is complexed with a bis-(dialkylphosphinoferrocene) ligand of formula 1. In this case, it has proved useful to add the palladium complex and bis-(dialkylphosphinoferrocene) ligand in a ratio of 1 to 10 up to 10 to 1, or 1:5 up to 5:1, in particular 2.5:1 up to 1:2.5, such as 2 to 1. The ratio refers to the molar quantities of palladium complex and bis-(dialkylphosphinoferrocene) ligand. This means, for example, that when 0.2 mol % of palladium complex are used, 0.1 mol % of bis-(dialkylphosphinoferrocene) ligand are added.

In the procedure described above, the additional quantity of bis-(dialkylphosphinoferrocene) ligand can, for example, be added to the catalyst solution, either before, during or after its production from the starting products and this can then be stored until the reaction is carried out.

As an alternative, the bis-(dialkylphosphinoferrocene) ligand, the primary aromatic amine A-NH$_2$, the aryl halide X-B and the base can also be introduced together provided with a solvent, and the catalyst solution can be added in the appropriate quantity.

Alternatively, however, a solid catalyst can also be produced from the catalyst solution. For this purpose, an additive is added to the catalyst solution, which additive forms a barely soluble, and easily crystallizing palladium complex. In so doing, a stoichiometric compound is precipitated. Under the precipitation conditions, that is with a sufficiently low solvent volume, this is sufficiently hard to dissolve to precipitate but soluble enough to be used again to produce a catalyst solution.

In the production of the palladium complex, the palladium atom, along with the bis-(dialkylphosphinoferrocene) ligand, is also complexed by ligands from the palladium compound used to produce the palladium complex, that is for example by 1,3-divinyl-1,1,3,3-tetramethyldisiloxane (also known as VTS or VS), bis(dibenzylideneacetone) (dba) or others.

However, these palladium complexes are easily soluble. The purpose of the additive is to complex the palladium atom and to thereby form a less soluble palladium complex that can be easily separated off and processed further. Naphthoquinone, maleic anhydride, maleimide, maleic acid diethyl ester or norbornene, in particular naphthoquinone or maleimide, for example, are suitable as additive. Barely soluble, easily crystallizing palladium complexes are then formed, which can be filtered off, washed and dried. In so doing, a stoichiometric compound is precipitated. Under the precipitation conditions, that is with a sufficiently low solvent volume, this is sufficiently hard to dissolve to precipitate but soluble enough to be used again to produce a catalyst solution which is suitable for providing the first and/or second catalyst.

Therefore, the present patent application also relates to the materials 1,1'-bis(diisopropylphosphino)ferrocene palladium(0)-maleimide [Pd(dippf)(maleimide)], 1,1'-bis(diisopropylphosphino)ferrocene palladium(0)-1,3-divinyl-1,1,3,3,-tetramethyldisiloxane [Pd(dippf)(VTS)], 1,1'-bis(diisopropylphosphino)ferrocene palladium(0)-bis(dibenzylideneacetone) [Pd(dippf)(dba)], 1,1'-bis(diisopropylphosphino)ferrocene palladium(0)-naphthoquinone [Pd(dippf)(naphthoquinone)], 1,1'-bis(diisopropylphosphino)ferrocene palladium(0)-maleic anhydride [Pd(dippf)(maleic anhydride)], 1,1'-bis(diisopropylphosphino)ferrocene palladium(0)-maleic acid diethyl ester [Pd(dippf)(maleic acid diethyl ester)], 1,1'-bis(diisopropylphosphino)ferrocene palladium(0)-norbornene [Pd(dippf)(norbornene)].

The palladium atom (palladium in the oxidation stage 0) is often coordinated three times and the complexes as a rule trigonally planar, so that compounds, such as 1,3-divinyl-1,1,3,3-tetramethyldisiloxane (VTS or VS) or bis(dibenzylideneacetone), which contain more than one double bond, only complex the palladium atom with one of its double bonds. The second double bond either doesn't complex or complexes a further palladium atom.

The structure of some of these compounds can be represented as follows:

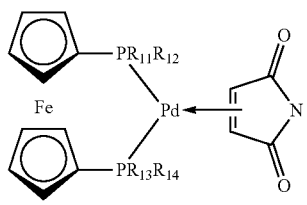

Formula 200

The moieties R11 to R14 can be the same or different in formula 200 as described above and are, in particular, alkyl moieties with one to five carbon atoms. If R11 to R14 are isopropyl moieties, formula 200 shows 1,1'-bis(diisopropylphosphino)ferrocene palladium(0)-maleimide [Pd(dippf)(maleimide)].

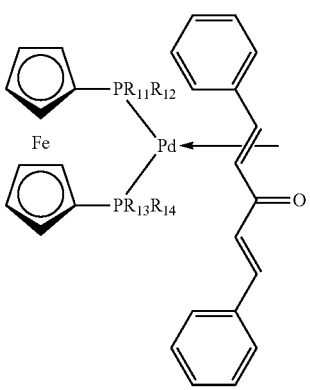

Formula 210

The moieties R11 to R14 can be the same or different in formula 210 as described above and are, in particular, alkyl moieties with one to five carbon atoms. If R11 to R14 are isopropyl moieties, formula 210 shows 1,1'-bis(diisopropylphosphino)ferrocene palladium(0)-bis(dibenzylideneacetone) [Pd(dippf)(dba)].

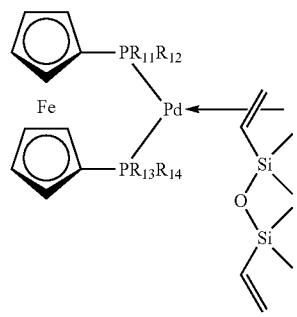

Formula 220

The moieties R11 to R14 can be the same or different in formula 220 as described above and are, in particular, alkyl moieties with one to five carbon atoms. If R11 to R14 are isopropyl moieties, formula 220 shows 1,1'-bis(diisopropylphosphino)ferrocene palladium(0)-1,3-divinyl-1,1,3,3,-tetramethyldisiloxane [Pd(dippf)(VTS)].

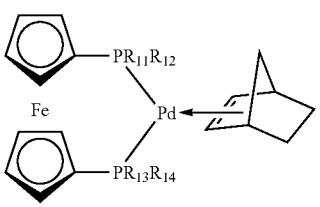

Formula 230

The moieties R11 to R14 can be the same or different in formula 230 as described above and are, in particular, alkyl moieties with one to five carbon atoms. If R11 to R14 are isopropyl moieties, formula 230 shows 1,1'-bis(diisopropylphosphino)ferrocene palladium(0)-norbornene [Pd(dippf)(norbornene)].

These solid palladium complexes can also, as described above, be used as catalyst, wherein they are introduced or added to the educts and the base as a solid or solution.

In an advantageous embodiment, the corresponding ligand, that is the bis-(dialkylphosphinoferrocene) ligand used in the solid palladium complex, is added along with the solid palladium complex.

In this case, it has proved useful to add the solid palladium complex and bis-(dialkylphosphinoferrocene) ligand in a ratio of 1 to 10 up to 10 to 1, or 1:5 up to 5:1, in particular 2.5:1 up to 1:2.5, such as 2 to 1. The ratio refers to the molar quantities of solid palladium complex and bis-(dialkylphosphinoferrocene) ligand. This means, for example, that when 0.2 mol % of solid complex are used, 0.1 mol % of bis-(dialkylphosphinoferrocene) ligand are added. However, the solid palladium complex can also be mixed with additional bis-(dialkylphosphinoferrocene) ligand in a solid state, thereby obtaining a powder mixture. This powder mixture is stable when stored and can be easily handled.

EXAMPLES

Example 1: Preparation of the Catalyst Solution 1,1'-bis(diisopropylphosphino)ferrocene (dippf) (213 mg, 0.50 mmol) was dissolved in diethyl ether (5 mL) and 1,3-divinyl-1,1,3,3-tetramethyldisiloxane palladium(0) (Pd-VTS) in 2,4,6,8-tetramethylcyclotetrasiloxane (0.50 mL, 0.50 mmol Pd) added drop by drop. The orange mixture was stirred for 1 hour at room temperature.

Example 2: Preparation of the Solid Catalyst [Pd(Dippf)(Maleimide)]

Initially, the process was carried out as in example 1. Then maleimide (99.1 mg, 1.00 mmol) was added to diethyl ether (5 mL) and treated in an ultrasonic bath for 10 minutes, whereupon a yellow precipitate was formed. After the solid had settled, the supernatant solution was removed and the residue washed with diethyl ether (3×5 mL). By drying in vacuum ($10^{-2}$ mbar), the desired palladium complex was able to be isolated as a yellow solid (291 mg, 0.47 mmol, 94%).

Analytical Data:

$^1$H NMR (400 MHz, dioxane-$d_8$): δ=7.84 (s, 1H, N—H), 4.44-4.39 (m, 6H, ferrocene-H), 4.37-4.33 (m, 2H, ferrocene-H), 2.53-2.40 (m, 2H), 2.35-2.20 (m, 2H), 1.34 (d, J=7.0 Hz, 3H), 1.30 (d, J=7.0 Hz, 3H), 1.26 (d, J=7.3 Hz, 3H), 1.22 (d, J=7.3 Hz, 6H), 1.18 (d, J=7.3 Hz, 3H), 1.13 (d, J=7.3 Hz, 3H), 1.09 ppm (d, J=7.3 Hz, 3H).

$^{31}$P-NMR (162 MHz, dioxane-$d_8$): δ=: 38.87 ppm (s, 2 P).

Example 3: Syntheses on a Preparative Scale

Diagram 1

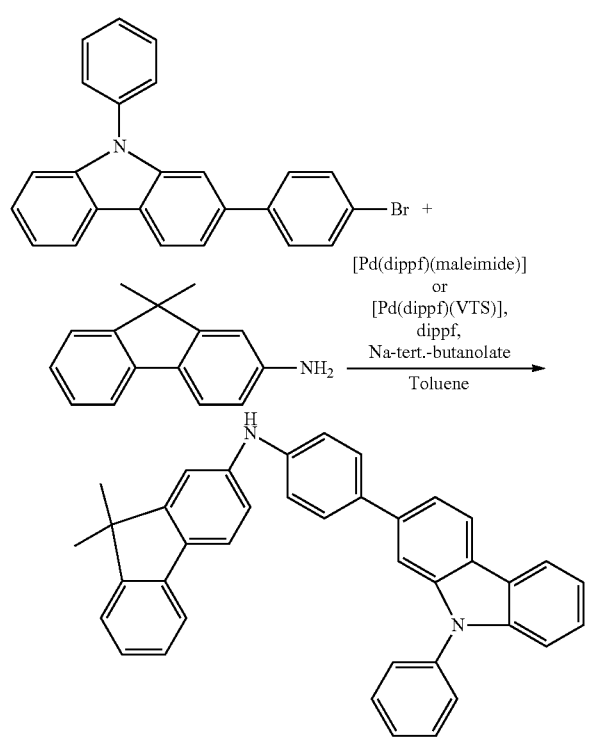

Example 3a: Use of [Pd(Dippf)(Maleimide)] as Palladium Complex

The aryl bromide 132 (7.97 g, 20.0 mmol), the amine 131 (4.17 g, 20.0 mmol), 1,1'-bis(diisopropylphosphino)ferrocene (8.5 mg, 0.02 mmol) and sodium-tert-butanolate (2.35 g, 24.0 mmol) were introduced in a dry three-necked flask with reflux condenser, gas inlet, relief valve, and magnetic stirring rod and brought under a nitrogen atmosphere by repeated evacuation and gassing. Toluene (30 mL) and [Pd(dippf)(maleimide)] (24.9 mg, 0.04 mmol, from example 2) were added to toluene (10 mL) and the mixture heated for 20 hours to 70° C. The reaction was followed by thin-layer chromatography and it was determined that after this period the full conversion was achieved. After cooling to room temperature, water (60 mL) was added and extracted using dichloromethane (150 mL). The organic phase was separated off, dried over magnesium sulfate (5 g) and filtered through basic aluminum oxide (10 g). The solvent was removed in the vacuum (40° C., 10 mbar) and the slightly yellow residue washed with diethyl ether (3×20 mL). After drying in vacuum (2 h, $10^{-2}$ mbar), the product was obtained as a colorless solid (10.2 g, 19.4 mmol, 97%).

$^1$H NMR (400 MHz, chloroform-d): Γ=8.41 (d, J=1.3 Hz, 1H), 8.26 (d, J=7.8 Hz, 1H), 7.75-7.60 (m, 9H), 7.55-7.44 (m, 5H), 7.41-7.21 (m, 6H), 7.13 (d, J=7.0 Hz, 1H), 5.91 (s, 1H), 1.55 ppm (s, 6H).

$^{13}$C NMR (101 MHz, chloroform-d): δ=155.3, 153.1, 142.6, 142.0, 141.3, 140.0, 139.3, 137.7, 134.6, 133.2, 132.5, 129.9 (2C), 128.1, 127.4 (2C), 127.0 (2C), 126.9, 126.0 (2C), 125.0, 123.9, 123.5 (2C), 122.4, 120.8, 120.3, 120.0, 119.9, 119.1, 118.1, 116.8, 112.2, 110.0, 109.9, 46.8, 27.2 ppm (2C).

Elemental analysis: calculated for $C_{39}H_{30}N_2$: C, 88.94, H, 5.74, N, 5.32; detected: C, 88.64, H, 5.91, N, 5.22.

Example 3b: Use of [Pd(Dippf)(VTS)] as a Palladium Complex

A catalyst stock solution similar to that described in example 1 prepared from 1,1'-bis(diisopropylphosphino) ferrocene (213.8 mg, 0.50 mmol), toluene (0.5 mL) and a mixture from 1,3-divinyl-1,1,3,3-tetramethyldisiloxane palladium(0) (Pd-VTS) in 2,4,6,8-tetramethylcyclotetrasiloxane (0.5 mL, 10.87% palladium), was used for this reaction. The mixture was stirred for one hour at room temperature.

The aryl bromide 132 (7.97 g, 20.0 mmol), the amine 131 (4.17 g, 20.0 mmol), and sodium-tert-butanolate (2.35 g, 24.0 mmol) were introduced in a dry three-necked flask with reflux condenser, gas inlet, relief valve, and magnetic stirring rod and brought under a nitrogen atmosphere by evacuation and gassing. Toluene (40 mL) and the catalyst stock solution (100 μL, 91.8 mg, 0.04 mmol palladium) were then added and the mixture heated for 20 hours to 70 CC. The reaction was followed by thin-layer chromatography and it was determined that the full conversion was achieved after this period. After cooling to room temperature, water (60 mL) was added and extracted using dichloromethane (150 mL). The organic phase was separated off, dried over magnesium sulfate (5 g) and filtered through basic aluminum oxide (10 g). The solvent was removed in vacuum (40° C., 10 mbar) and the slightly yellow residue washed with ether (3×20 mL). After drying in vacuum (2 h, $10^{-2}$ mbar), the product was obtained as a colorless solid (9.71 g, 18.4 mmol, 92%).

The reaction equation is shown in diagram 1. A repeated arylation of the primary amine 131 by the aryl bromide 132 was not observed in any of the examples.

Examples 4a to 4i

General Rule:

All tests were carried out in 20 mL headspace vials for the gas chromatography, which vials were sealed with aluminum flange caps with teflon-coated butyl rubber septa (both available, for example, from VWR). To control the temperatures of the vessels, 8 cm-high cylindrical aluminum blocks were used, the diameter of which exactly corresponds to that of the hot plates of laboratory magnetic stirrers (e.g. Heidolph Mr 2002). These aluminum blocks were provided with ten 7 cm deep holes with the diameter of the reaction vessels and a hole for accommodating a temperature sensor.

To enable the simultaneous evacuation and refilling of ten vessels, vacuum distributors were manufactured for connection to the Schlenk line. To this end, ten 3 mm vacuum-tight teflon hoses were respectively connected at one end to adapters to accommodate Luer Lock syringe needles and at the other end to a steel tube that can be connected to the Schlenk line via a vacuum hose.

To carry out the tests, the aryl bromide (1.00 mmol), the corresponding primary amine (1.00 mmol) and sodium-tert-butanolate (118 mg, 1.20 mmol) were weighed out in air into the reaction vessels, 20 mm magnetic stirring bars were added and the vessels were sealed airtight with septa caps using flanging pliers. 10 reaction vessels were respectively inserted into the holes of an aluminum block and connected to the vacuum distributor via cannulas, which were bored through the septa caps.

The reaction vessels were then collectively evacuated and flushed with nitrogen three times in succession. After the reaction vessels were provided with an inert gas atmosphere in this way, a pressure equalization with the outside atmosphere was created in the vacuum line via the relief valve. A stock solution of [Pd(dippf)(maleimide)] (1.24 mg, 0.002 mmol) and dippf (0.85 mg, 0.002 mmol) in toluene (2 mL) was injected through the septa caps with the aid of a syringe. The aluminum block was then brought to 70° C. and the needles were removed from the vacuum distributor.

After a reaction time of 20 hours, the vessels were carefully opened after cooling and the reaction medium was diluted with dichloromethane (30 mL) and water (30 mL). The aqueous phase was set to pH=7 with 1N hydrochloric acid, separated from the organic phase and extracted with dichloromethane (2×20 mL). The combined organic phases were dried over magnesium sulfate, filtered and then investigated using thin layer chromatography.

The solvent was removed in vacuum (40° C., 500 mbar) and the remaining raw product was cleaned using column chromatography (basic $Al_2O_3$, diethyl ether:hexane or ethylacetate:hexane).

Example 4a: Synthesis of Compound 3a

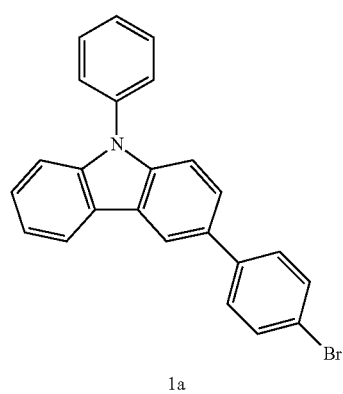

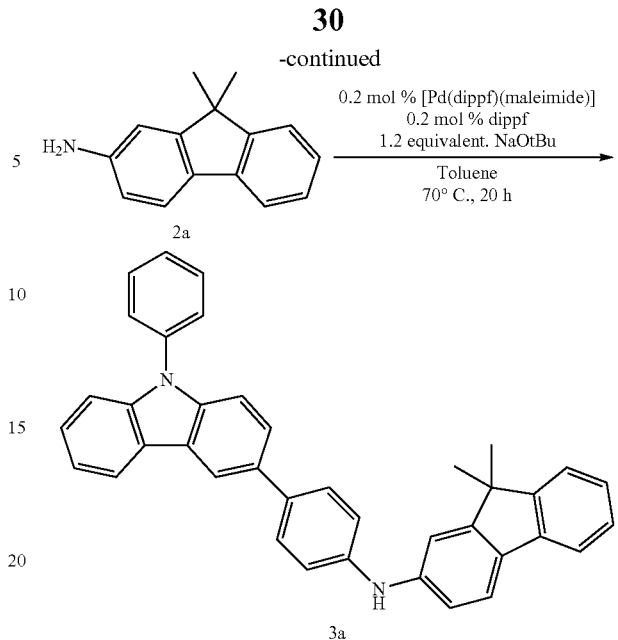

In accordance with the general rule, compound 3a was synthesized starting with 1a (398 mg, 1.00 mmol) and 2a (209 mg, 1.00 mmol) and was able to be isolated using column chromatography ($Al_2O_3$, diethyl ether:hexane=1:1) in 94% yield (496 mg, 0.94 mmol). $^1$H NMR (400 MHz, chloroform-d): δδ=8.41 (d, J=1.3 Hz, 1H), 8.26 (d, J=7.8 Hz, 1H), 7.75-7.60 (m, 9H), 7.55-7.44 (m, 5H), 7.41-7.21 (m, 6H), 7.13 (d, J=7.0 Hz, 1H), 5.91 (s, 1H), 1.55 ppm (s, 6H). $^{13}$C NMR (101 MHz, chloroform-d): δδ=155.3, 153.1, 142.6, 142.0, 141.3, 140.0, 139.3, 137.7, 134.6, 133.2, 132.5, 129.9 (2C), 128.1, 127.4 (2C), 127.0 (2C), 126.9, 126.0 (2C), 125.0, 123.9, 123.5 (2C), 122.4, 120.8, 120.3, 120.0, 119.9, 119.1, 118.1, 116.8, 112.2, 110.0, 109.9, 46.8, 27.2 ppm (2C), CHN: calculated for $C_{39}H_{30}N_2$: C, 88.94, H, 5.74, N, 5.32; detected: C, 88.79, H, 5.86, N, 5.19.

Example 4b: Synthesis of Compound 3b

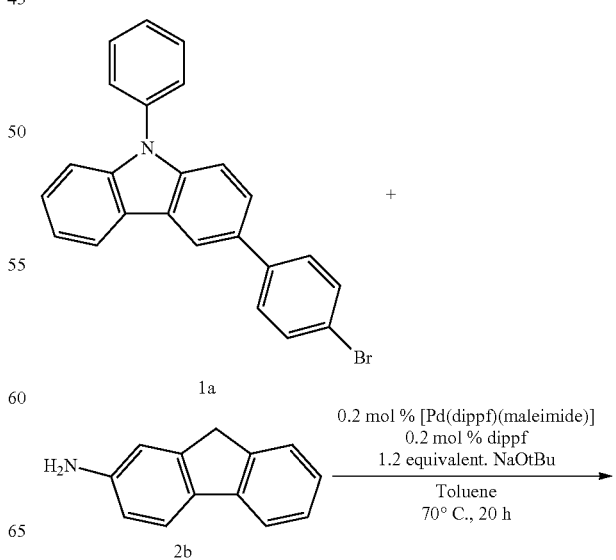

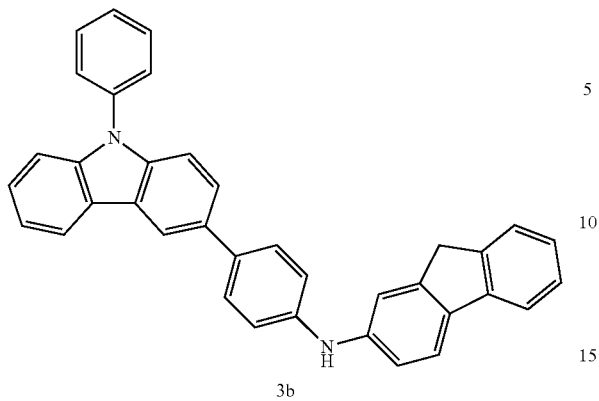

3b

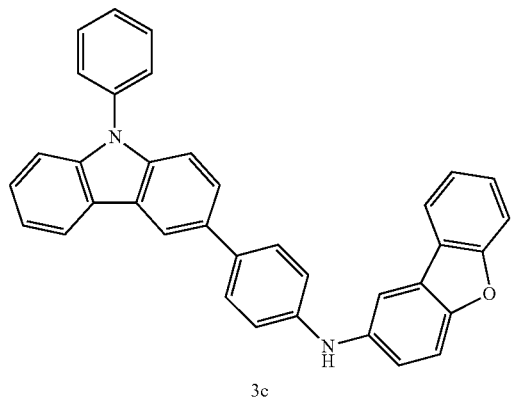

3c

In accordance with the general rule, compound 3b was synthesized starting with 1a (398 mg, 1.00 mmol) and 2b (181 mg, 1.00 mmol) and was able to be isolated using column chromatography ($Al_2O_3$, diethyl ether:hexane=1:1) in 92% yield (460 mg, 0.92 mmol). $^1$H NMR (400 MHz, DMSO-$d_6$): δ=8.54 (d, J=1.5 Hz, 1H), 8.44 (s, 1H), 8.35 (d, J=7.8 Hz, 1H), 7.77-7.63 (m, 9H), 7.55 (m, 1H), 7.51 (d, J=7.5 Hz, 1H), 7.47-7.36 (m, 4H), 7.31 (m, 2H), 7.26 (d, J=8.8 Hz, 2H), 7.20 (dt, J=7.5 Hz, 1.3 Hz, 1H), 7.15 (dd, J=8.3 Hz, 2.0 Hz, 1H), 3.87 ppm (s, 2H). $^{13}$C NMR (101 MHz, DMSO-$d_6$): δ=144.6, 142.7, 142.3, 142.2, 141.5, 140.5, 139.1, 136.9, 133.3, 132.6, 132.2, 130.2 (2C), 127.6, 127.5 (2C), 126.7, 126.6 (2C), 126.4, 125.3, 124.9, 124.7, 123.4, 123.0, 120.8, 120.7, 120.1, 118.8, 117.6, 117.4 (2C), 117.3, 115.9, 113.1, 110.0, 109.7 ppm. CHN: calculated for $C_{37}H_{26}N_2$: C, 89.13, H, 5.26, N, 5.62; detected: C, 88.83, H, 5.25, N, 5.54.

In accordance with the general rule, compound 3c was synthesized starting with 1a (398 mg, 1.00 mmol) and 2c (183 mg, 1.00 mmol) and was able to be isolated using column chromatography ($Al_2O_3$, diethyl ether:hexane=1:1) in 88% yield (442 mg, 0.88 mmol). $^1$H NMR (400 MHz, DMSO-$d_6$): δ=8.72 (s, 1H), 8.55 (d, J=1.5 Hz, 1H), 8.35 (d, J=7.8 Hz, 1H), 7.99-7.93 (m, 2H), 7.77-7.62 (m, 7H), 7.60 (d, J=8.0 Hz, 1H), 7.54 (m, 1H), 7.47-7.27 (m, 9H), 7.16 ppm (dd, J=8.5 Hz, 1.8 Hz, 1H). $^{13}$C NMR (101 MHz, DMSO-$d_6$): δ=157.1, 155.3, 144.0, 141.6, 140.5, 139.2, 136.9, 133.0, 132.5, 130.2 (2C), 127.6, 127.5 (2C), 126.6 (2C), 126.4, 125.6, 124.7, 124.2, 123.4, 123.0 (2C), 121.6, 120.8, 120.1, 119.7, 118.0 (2C), 117.7, 115.5, 113.1, 111.2, 110.0, 109.7, 97.9 ppm. CHN: calculated for $C_{36}H_{24}N_2O$: C, 86.38, H, 4.83, N, 5.60; detected: C, 86.02, H, 5.04, N, 5.43.

Example 4c: Synthesis of Compound 3c

Example 4c: Synthesis of Compound 3d

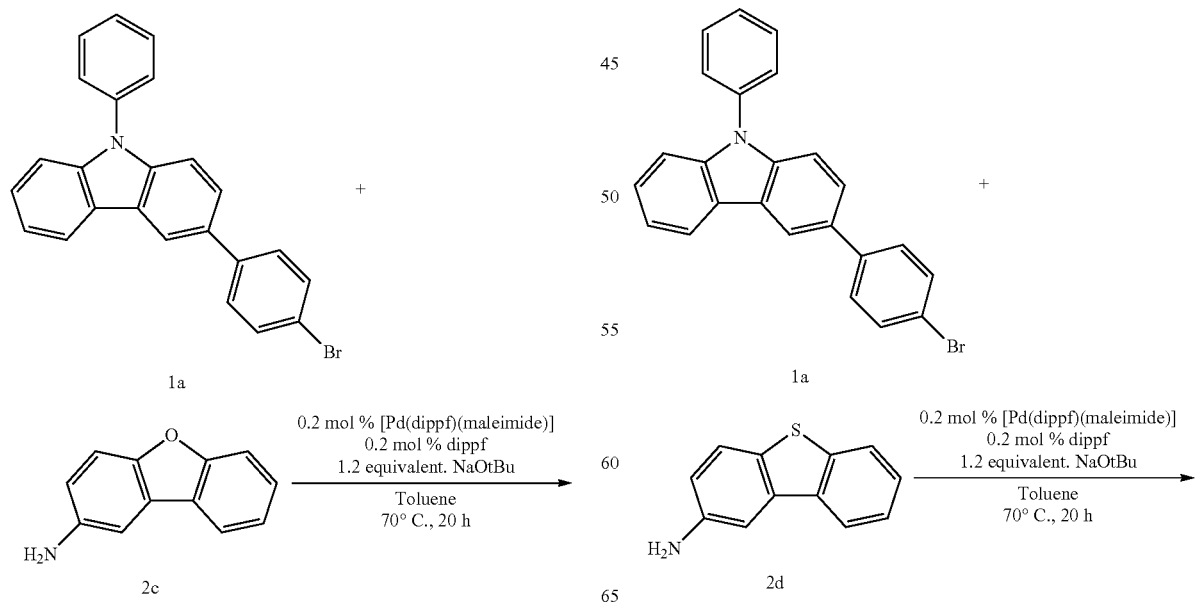

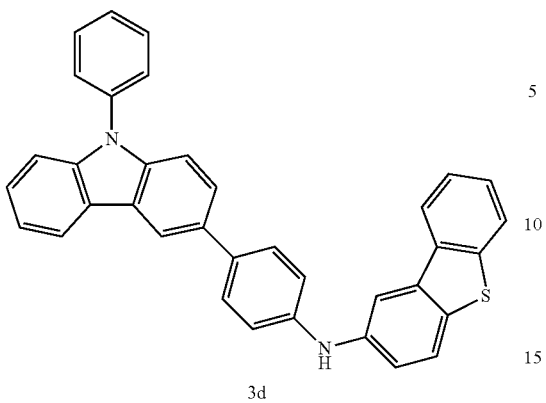

3d

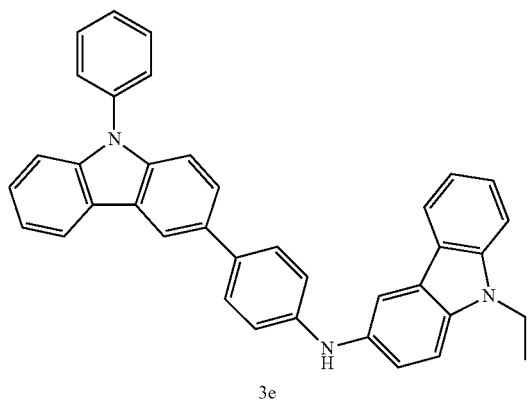

3e

In accordance with the general rule, compound 3d was synthesized starting with 1a (398 mg, 1.00 mmol) and 2d (199 mg, 1.00 mmol) and was able to be isolated using column chromatography (Al$_2$O$_3$, diethyl ether:hexane=1:1) in 96% yield (496 mg, 0.96 mmol). $^1$H NMR (400 MHz, DMSO-d$_6$): δ=8.54 (d, J=1.5 Hz, 1H), 8.51 (s, 1H), 8.35 (d, J=7.5 Hz, 1H), 8.25 (m, 1H), 8.07 (d, J=2.0 Hz, 1H), 7.99 (m, 1H), 7.89 (d, 2.5 J=8.5 Hz, 1H), 7.75-7.63 (m, 7H), 7.55 (m, 1H), 7.48 (m, 2H), 7.45-7.37 (3H), 7.36-7.27 ppm (m, 4H). $^{13}$C NMR (101 MHz, DMSO-d$_6$): δ=142.7, 141.0, 140.5, 139.5, 139.1, 136.9, 136.0, 134.9, 132.6, 132.1, 130.2 (2C), 129.7, 127.6, 127.5 (2C), 126.9, 126.6 (2C), 126.4, 124.7, 124.5, 123.6, 123.4, 123.1, 123.0, 121.9, 120.8, 120.1, 119.0, 117.6, 116.8 (2C), 110.0, 109.7, 109.2 ppm. CHN: calculated for C$_{36}$H$_{24}$N$_2$S: C, 83.69, H, 4.68, N, 5.42, S 6.21; detected: C, 83.40, H, 4.76, N, 5.35, S 6.31.

Example 4d: Synthesis of Compound 3e

In accordance with the general rule, compound 3e was synthesized starting with 1a (398 mg, 1.00 mmol) and 2e (221 mg, 1.00 mmol) and was able to be isolated using column chromatography (Al$_2$O$_3$, ethyl acetate:hexane=1:2) in 95% yield (502 mg, 0.95 mmol). $^1$H NMR (400 MHz, DMSO-d$_6$): δ=8.50 (d, J=1.5 Hz, 1H), 8.33 (d, J=7.8 Hz, 1H), 8.14 (s, 1H), 8.11 (d, J=7.5 Hz, 1H), 7.96 (d, J=2.0 Hz, 1H), 7.72-7.61 (m, 7H), 7.58-7.51 (m, 3H), 7.46-7.37 (m, 4H), 7.35-7.27 (m, 2H), 7.17-7.11 (m, 3H), 4.41 (q, J=7.0 Hz, 2H), 1.31 ppm (t, J=7.0 Hz, 3H), $^{13}$C NMR (101 MHz, DMSO-d$_6$): δ=144.6, 142.7, 142.3, 142.2, 141.5, 140.5, 139.1, 136.9, 133.3, 132.6, 132.2, 130.2 (2C), 127.6, 127.5 (2C), 126.7, 126.6 (2C), 126.4, 125.3, 124.9, 124.7, 123.4, 123.0, 120.8, 120.7, 120.1, 118.8, 117.6, 117.4 (2C), 117.3, 115.9, 113.1, 110.0, 109.7, 36.5 ppm. CHN: calculated for C$_{38}$H$_{29}$N$_3$: C, 86.50, H, 5.54, N, 7.96; detected: C, 86.32, H, 5.63, N, 7.90.

Example 4e: Synthesis of Compound 3f

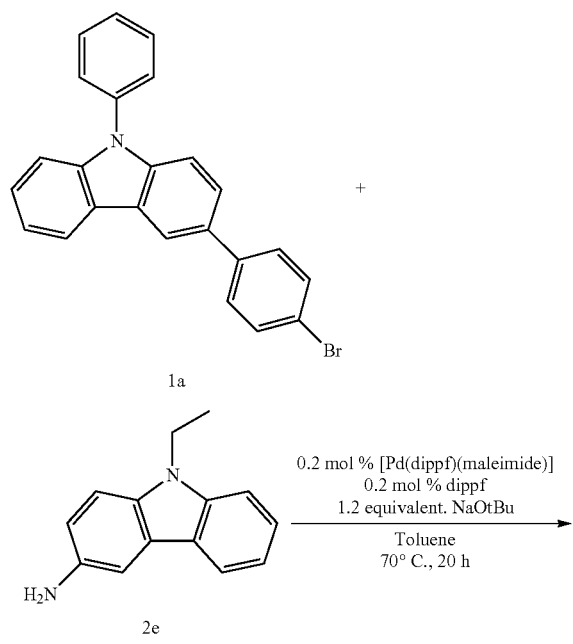

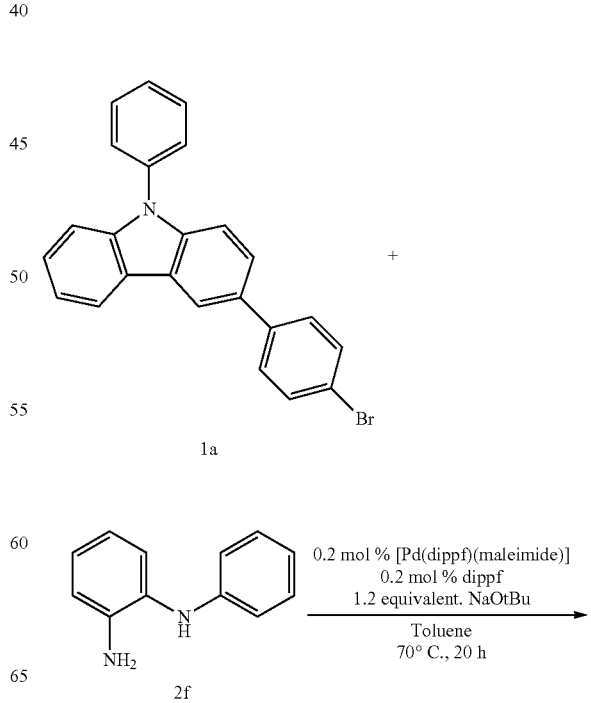

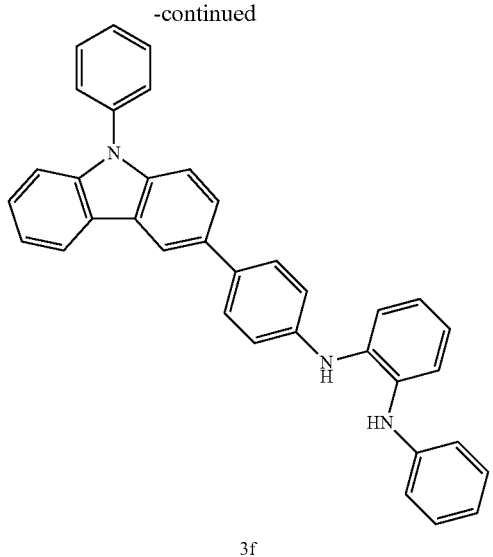

3f

In accordance with the general rule, compound 3f was synthesized starting with 1a (398 mg, 1.00 mmol) and 2f (188 mg, 1.00 mmol) and was able to be isolated using column chromatography (Al$_2$O$_3$, ethyl acetate:hexane=1:2) in 84% yield (423 mg, 0.84 mmol). $^1$H NMR (400 MHz, DMSO-d$_6$): δ=8.49 (d, J=1.5 Hz, 1H), 8.33 (d, J=7.8 Hz, 1H), 7.72-7.61 (m, 7H), 7.53 (m, 1H), 7.46-7.37 (m, 4H), 7.36 (s, 1H), 7.34-7.26 (m, 3H), 7.19 (m, 2H), 7.10 (d, J=8.5 Hz, 2H), 6.99 (dd, J=8.7 Hz, 0.9 Hz, 2H), 6.94 (m, 2H), 6.76 ppm (m, 1H). $^{13}$C NMR (101 MHz, DMSO-d$_6$): δ=144.5, 143.4, 140.5, 139.0, 136.9, 134.6 (2C), 132.7, 131.6, 130.2 (2C), 129.0 (2C), 127.6, 127.3 (2C), 126.6 (2C), 126.3, 124.6, 123.4, 123.0, 122.1, 122.0, 120.8, 120.1, 119.9 (2C), 119.0, 117.5, 116.7 (2C), 116.2 (2C), 109.9, 109.6 ppm. CHN: calculated for C$_{36}$H$_{27}$N$_3$: C, 86.20, H, 5.43, N, 8.38; detected: C, 85.82, H, 5.62, N, 8.22.

Example 4f: Synthesis of Compound 3g

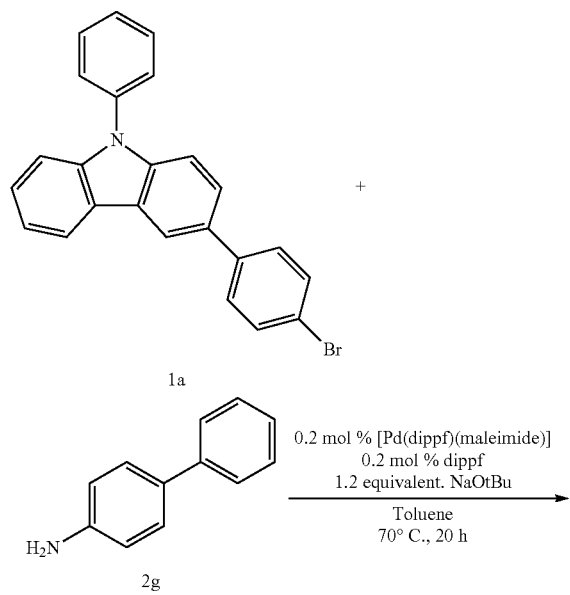

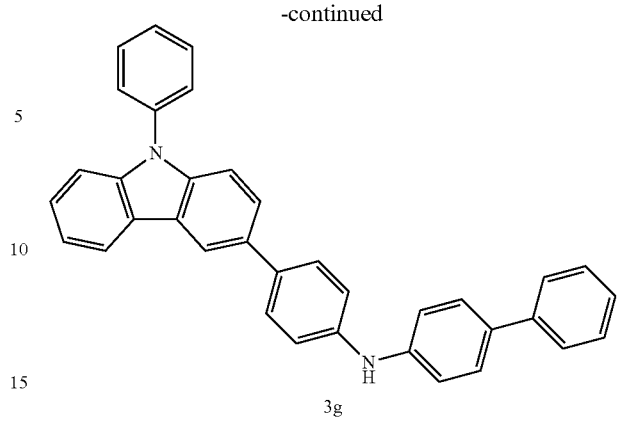

3g

In accordance with the general rule, compound 3g was synthesized starting with 1a (398 mg, 1.00 mmol) and 2g (169 mg, 1.00 mmol) and was able to be isolated using column chromatography (Al$_2$O$_3$, diethyl ether:hexane=1:1) in 95% yield (462 mg, 0.95 mmol). $^1$H NMR (400 MHz, DMSO-d$_6$): δ=8.53 (d, J=1.3 Hz, 1H), 8.47 (s, 1H), 8.35 (d, J=7.5 Hz, 1H), 7.74-7.53 (m, 12H), 7.47-7.38 (m, 5H), 7.34-7.19 ppm (m, 6H). $^{13}$C NMR (101 MHz, DMSO-d$_6$): δ=143.0, 142.9, 141.9, 140.5, 140.1, 139.1, 136.9, 132.6, 132.5, 131.2, 130.2 (2C), 128.9 (2C), 127.6, 127.5 (2C), 127.4 (2C), 126.6 (2C), 126.4 (2C), 125.8 (2C), 124.7, 123.4, 123.0, 120.8, 120.1, 117.7, 117.5 (2C), 116.8, 110.0, 109.7 ppm. CHN: calculated for C$_{36}$H$_{26}$N$_2$: C, 88.86, H, 5.39, N, 5.76; detected: C, 88.49, H, 5.39, N, 5.68.

Example 4g: Synthesis of Compound 3i

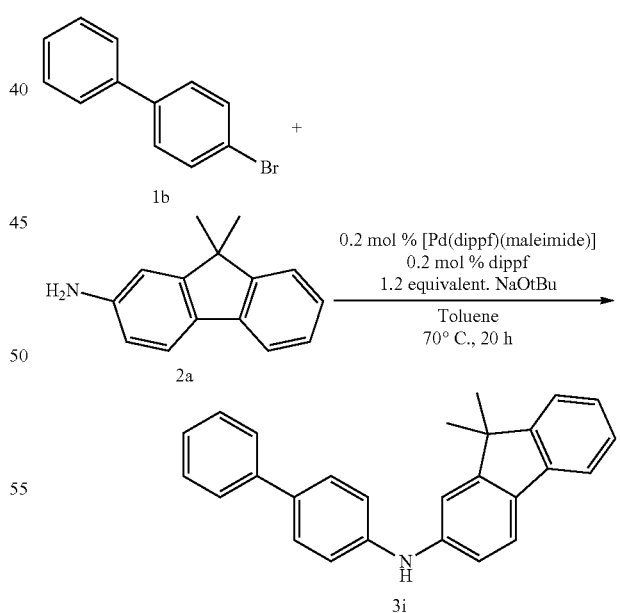

In accordance with the general rule, compound 3i was synthesized starting with 1 b (259 mg, 1.00 mmol) and 2a (209 mg, 1.00 mmol) and was able to be isolated using column chromatography (Al$_2$O$_3$, diethyl ether:hexane=1:2) in 89% yield (323 mg, 0.89 mmol). $^1$H NMR (400 MHz, chloroform-d): δ=7.72-7.63 (m, 4H), 7.59 (m, 2H), 7.51-

7.44 (m, 3H), 7.37 (m, 2H), 7.32 (t, J=7.0 Hz, 1H), 7.25 (br. s, 1H), 7.22 (d, J=8.3 Hz, 2H), 7.13 (br. d, J=7.5 Hz, 1H), 5.92 (br. s, 1H), 1.54 ppm (s, 6H). $^{13}$C NMR (101 MHz, chloroform-d): δ=155.3, 153.1, 142.7, 142.1, 140.8, 139.2, 133.5, 132.8, 128.7 (2C), 128.0 (2C), 126.9, 126.6, 126.5 (2C), 126.1, 122.4, 120.8, 119.1, 117.6 (2C), 117.2, 112.6, 46.8, 27.2 ppm (2O). CHN: calculated for $C_{27}H_{23}N$: C, 89.71, H, 6.41, N, 3.87; detected: C, 89.69, H, 6.27, N, 3.84.

Example 4h: Synthesis of Compound 3j

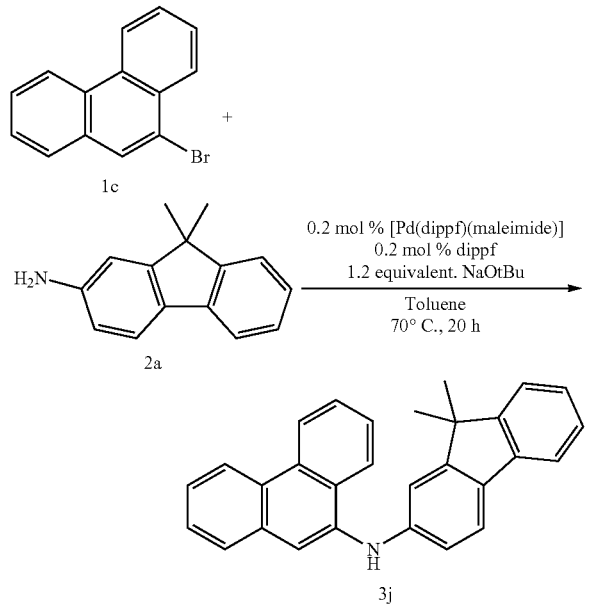

In accordance with the general rule, compound 3j was synthesized starting with 1c (268 mg, 1.00 mmol) and 2a (209 mg, 1.00 mmol) and was able to be isolated using column chromatography (Al$_2$O$_3$, diethyl ether:hexane=1:2) in 87% yield (335 mg, 0.87 mmol). $^1$H NMR (400 MHz, DMSO-d$_6$): δ=8.86 (m, 1H), 8.72 (m, 1H), 8.42 (s, 1H), 8.37 (dd, J=8.2 Hz, 1.1 Hz, 1H), 7.77-7.65 (m, 5H), 7.63 (s, 1H), 7.51 (m, 2H), 7.45 (d, J=7.5 Hz, 1H), 7.32 (d, J=2.0 Hz, 1H), 7.27 (dt, J=7.5 Hz, 1.1 Hz, 1H), 7.20 ((it, J=7.3 Hz, 1.0 Hz, 1H), 7.13 (dd, J=8.3 Hz, 2.0 Hz, 1H), 1.40 ppm (s, 6H). $^{13}$C NMR (101 MHz, DMSO-d$_6$): δ=154.7, 152.7, 144.6, 139.0, 137.8, 132.5, 131.0, 130.8, 127.5, 127.1, 127.1, 127.0, 126.9, 126.6, 126.4, 125.8, 124.5, 123.3, 123.3, 122.6, 122.5, 120.9, 118.9, 116.8, 112.4, 111.7, 46.3, 27.1 ppm (2C). CHN: calculated for $C_{29}H_{23}N$: C, 90.35, H, 6.01, N, 3.63; detected: C, 89.98, H, 6.31, N, 3.49.

Example 4i: Synthesis of Compound 3k

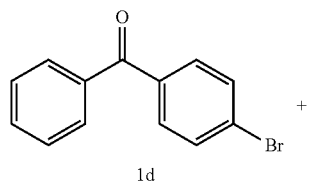

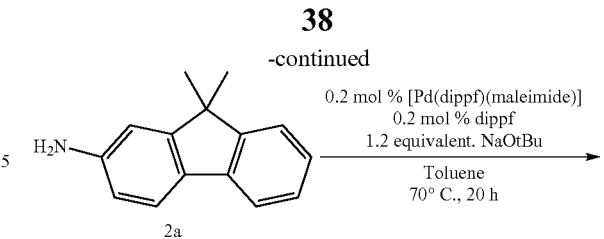

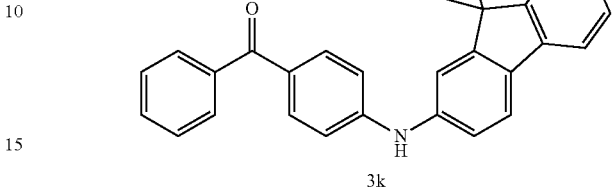

In accordance with the general rule, compound 3k was synthesized starting with 1d (269 mg, 1.00 mmol) and 2a (209 mg, 1.00 mmol) and was able to be isolated using column chromatography (Al$_2$O$_3$, diethyl ether:hexane=2:1) in 76% yield (296 mg, 0.76 mmol). $^1$H NMR (400 MHz, DMSO-d$_6$): δ=9.08 (s, 1H), 7.80-7.45 (m, 10H), 7.41-7.35 (m, 1H), 7.33-7.13 (m, 5H), 1.43 ppm (s, 6H). $^{13}$C NMR (101 MHz, DMSO-d$_6$): δ=193.6, 154.8, 152.9, 148.7, 140.6, 138.5 (2C), 132.9, 132.4 (2C), 131.5, 129.0 (2C), 128.3 (2C), 127.0, 126.7, 126.4, 122.6, 120.9, 119.3, 118.6, 114.1, 113.9 (2C), 46.4, 26.9 ppm (2O). CHN: calculated for $C_{28}H_{23}NO$: C, 86.34, H, 5.95, N, 3.60; detected: C, 86.05, H, 6.10, N, 3.52.

Examples 5a to 5h

General Rule for Preparing Tertiary Amines

All tests were carried out in 20 mL headspace vials for the gas chromatography, which vials were sealed with aluminum flange caps with teflon-coated butyl rubber septa (both available, for example, from VWR). To control the temperatures of the vessels, 8 cm-high cylindrical aluminum blocks were used, the diameter of which exactly corresponds to that of the hot plates of laboratory magnetic stirrers (e.g. Heidolph Mr 2002). These aluminum blocks were provided with ten 7 cm deep holes with the diameter of the reaction vessels and a hole for accommodating a temperature sensor.

To enable the simultaneous evacuation and refilling of ten vessels, vacuum distributors were manufactured for connection to the Schlenk line. To this end, ten 3 mm vacuum-tight teflon hoses were respectively connected at one end to adapters to accommodate Luer Lock syringe needles and at the other end to a steel tube that can be connected to the Schlenk line via a vacuum hose.

To carry out the tests, the first aryl bromide, X-B, (1.00 mmol), the corresponding primary amine, A-NH$_2$, (1.00 mmol) and sodium-feat-butanolate (118 mg, 1.20 mmol) were weighed out in air into the reaction vessels, 20 mm magnetic stirring bars were added and the vessels were sealed airtight with septa caps using flanging pliers. 10 reaction vessels were respectively inserted into the holes of an aluminum block and connected to the vacuum distributor via cannulas, which were bored through the septa caps.

The reaction vessels were then collectively evacuated and flushed with nitrogen three times in succession. After the reaction vessels were provided with an inert gas atmosphere in this way, a pressure equalization with the outside atmosphere was created in the vacuum line via the relief valve. A stock solution of [Pd(dippf)(maleimide)] (3.11 mg, 0.005 mmol) and dippf (2.13 mg, 0.005 mmol) in dry toluene (2 mL) was injected through the septa caps with the aid of a syringe. The aluminum block was then brought to 80° C. and the needles were removed from the vacuum distributor.

After a reaction time of 20 h, the second aryl bromide, X-C, (1.10 mmol) in dry toluene (0.5 mL) was injected through the septa caps. The temperature was increased to 120° C., the reaction mixture was stirred for 24 hours and opened carefully after cooling to room temperature, and the reaction medium diluted with dichloromethane (30 mL) and water (30 mL). The aqueous phase was separated from the organic phase and extracted with dichloromethane (2×20 mL). The combined organic phases were dried over magnesium sulfate, filtered and the solvent removed in vacuum (40° C., 500 mbar). The remaining raw product was cleaned using column chromatography (SiO$_2$, ethyl acetate:hexane) and the corresponding tertiary amine thereby obtained.

Example 5a: Preparation of Compound 4b

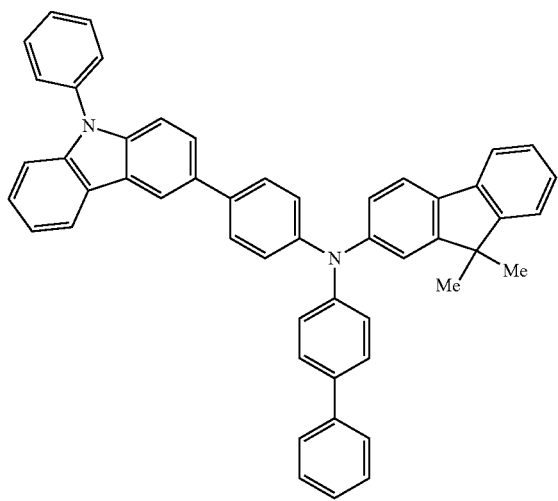 [SMILES: CC1(C)c2ccccc2-c2ccc(N(c3ccc(-c4ccccc4)cc3)c3ccc(-c4ccc5c(c4)c4ccccc4n5-c4ccccc4)cc3)cc21]

Compound 4b was obtained in accordance with the general rule, starting with 3-(4-bromophenyl)-9-phenyl-9H-carbazole (398 mg, 1 mmol), 9,9-dimethyl-9H-fluorene-2-amine (209 mg, 1 mmol) and 4-bromine-1,1'-biphenyl (262 mg, 1.10 mmol) as second aryl halide X-C. The compound was obtained as a beige solid (624 mg, 0.92 mmol, 92%) using column chromatography (hexane:ethyl acetate 4:1). Melting point; 155-156° C. $^1$H NMR (400 MHz, DMSO-d$_6$) δ=5.58 (d, J=1.5 Hz, 1H), 8.34 (d, J=7.8 Hz, 1H), 7.79-7.60 (m, 13H), 7.54 (m, 2H), 7.47-7.37 (m, 5H), 7.36-7.24 (m, 5H), 7.19 (d, J=8.8 Hz, 2H), 7.15 (d, J=8.5 Hz, 2H), 7.06 (dd, J=8.0 Hz, 2.0 Hz, 1H), 1.39 ppm (s, 6H); $^{13}$C NMR (101 MHz, DMSO-d$_6$) δ=154.9, 153.2, 146.8, 146.4, 145.9, 140.6, 139.5, 139.4, 138.2, 136.8, 135.4, 134.1, 134.1, 132.0, 130.2 (2C), 128.9 (2C), 127.7 (2C), 127.7, 127.6 (2C), 127.1, 127.0, 126.7, 126.6 (2C), 126.4, 126.2 (2C), 124.9, 124.3, 123.6, 123.4, 123.4 (2C), 122.9, 122.7, 121.2, 120.8, 120.2, 119.6, 118.8, 118.2, 110.0, 109.7, 99.5, 46.5, 26.8 ppm (20); IR v=1599 (m), 1484 (s), 1474 (s), 1458 (s), 1449 (vs), 1298 (m), 1232 (s), 760 (s), 735 (vs), 696 cm$^{-1}$ (vs); CHN: calculated (%) for O$_{51}$H$_{38}$N$_2$: C, 90.23, H, 5.64, N, 4.13; detected: C, 90.27, H, 5.46, N, 4.10.

Example 5b: Preparation of Compound 4c

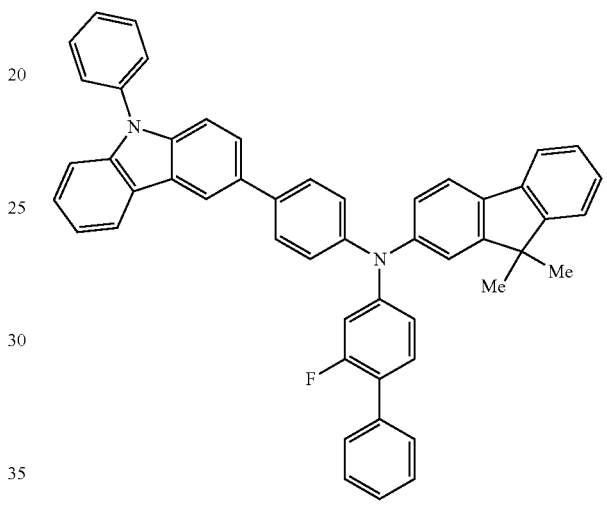

Compound 4c was obtained in accordance with the general rule, starting with 3-(4-bromophenyl)-9-phenyl-9H-carbazole (398 mg, 1 mmol), 9,9-dimethyl-9H-fluorene-2-amine (209 mg, 1 mmol) and 4-bromo-2-fluoro-1,1'-biphenyl (282 mg, 1.10 mmol) as second aryl halide X-C. The compound was obtained as a beige solid (655 mg, 0.94 mmol, 94%) using column chromatography (hexane:ethyl acetate 9:1). Melting point: 171-172° C. $^1$H NMR (400 MHz, DMSO-d$_6$) δ=8.58 (d, J=1.5 Hz, 1H), 8.33 (d, J=7.8 Hz, 1H), 7.77 (m, 4H), 7.69 (m, 3H), 7.62 (m, 2H), 7.53 (m, 4H), 7.46-7.22 (m, 13H), 7.1 (dd, J=8.3 Hz, 2.0 Hz, 1H), 6.89 (dd, J=8.5 Hz, 2.3 Hz, 1H), 6.82 (dd, J=13.3 Hz, 2.3 Hz, 1H), 1.39 ppm (s, 6H); $^{13}$C NMR (101 MHz, DMSO-d$_6$) δ=159.5 (d, J=245.8 Hz, 10), 155.1, 153.3, 148.5 (d, J=10.3 Hz, 10), 145.6, 145.1, 140.6, 139.5, 138.1, 136.8, 136.4, 135.0, 135.0 (d, J=1.5 Hz, 1C), 131.8, 131.2 (d, J=5.9 Hz, 1C), 130.2 (2C), 128.6 (2C), 128.4 (d, J=3.7 Hz, 2C), 127.9 (2C), 127.7, 127.3, 127.1, 127.0, 126.6 (2C), 126.5, 125.1 (2C), 125.0, 124.4, 123.4, 122.9, 122.7, 121.4, 121.0 (d, J=13.9 Hz, 1C), 120.8, 120.2, 119.8, 119.7, 118.3, 117.7 (d, J=1.5 Hz, 1C), 110.0, 109.7, 108.4 (d, J=25.7 Hz, 10), 46.6, 26.7 ppm (2C); $^{19}$F NMR (376.5 MHz, DMSO-d$_6$) δ=−116.70 ppm (s, 1F); IR v=1600 (m), 1501 (m), 1474 (s), 1458 (s), 1449 (s), 1310 (m), 1232 (m), 759 (s), 736 (s), 696 cm$^{-1}$ (vs); CHN: calculated (%) for C$_{51}$H$_{37}$FN$_2$: C, 87.9, H, 5.35, N, 4.02; detected: C, 87.77, H, 5.50, N, 3.93.

Example 5c: Preparation of Compound 4d

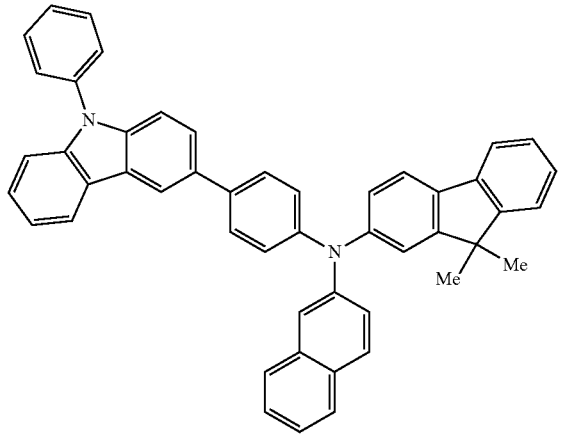 [SMILES: CC1(C)c2ccccc2-c2ccc(N(c3ccc(-c4ccc5c(c4)c4ccccc4n5-c4ccccc4)cc3)c3ccc4ccccc4c3)cc21]

Compound 4c was obtained in accordance with the general rule, starting with 3-(4-bromophenyl)-9-phenyl-9H-carbazole (398 mg, 1 mmol), 9,9-dimethyl-9H-fluorene-2-amine (209 mg, 1 mmol) and 2-bromonaphthaline (230 mg, 1.10 mmol) as second aryl halide X-C. The compound was obtained as a beige solid (628 mg, 0.96 mmol, 96%) using column chromatography (hexane:ethyl acetate 9:1). Melting point: 196-197° C. $^1$H NMR (400 MHz, DMSO-$d_6$) δ=8.58 (m, 1H), 8.33 (d, J=7.8 Hz, 1H), 7.84 (m, 2H), 7.77-7.60 (m, 10H), 7.57-7.47 (m, 3H), 7.46-7.35 (m, 5H), 7.34 (d, J=2.0 Hz, 1H), 7.33-7.23 (m, 4H), 7.19 (d, J=8.5 Hz, 2H), 7.05 (dd, J=8.3 Hz, 2.0 Hz, 1H), 1.36 ppm (s, 6H); $^{13}$C NMR (101 MHz, DMSO-$d_6$) δ=154.9, 153.2, 146.6, 146.1, 145.0, 140.6, 139.4, 138.3, 136.8, 135.4, 134.1, 134.0, 131.9, 130.2 (2C), 129.7, 129.1, 127.7 (2C), 127.7, 127.5, 127.1, 126.9, 126.7, 126.6 (2C), 126.5, 126.4, 124.9, 124.6, 124.2 (2C), 124.0, 123.4, 123.3, 122.9, 122.7, 121.2, 120.8, 120.2, 119.6 (2C), 118.5, 118.2, 110.0, 109.7, 46.5, 26.7 ppm (20); IR v=1597 (m), 1501 (m), 1458 (s), 1449 (s), 1299 (m), 1229 (m), 807 (m), 745 (s), 735 (vs), 697 cm$^{-1}$ (m); CHN: calculated (%) for $C_{49}H_{36}N_2$: C, 90.15, H, 5.56, N, 4.29; detected: C, 89.93, H, 5.70, N, 4.14.

Example 5d: Preparation of Compound 4e

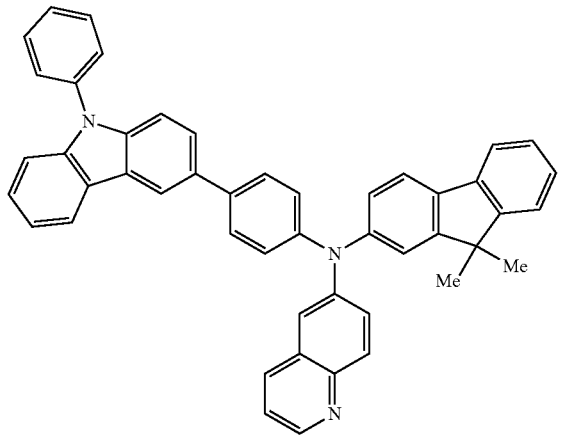 [SMILES: CC1(C)c2ccccc2-c2ccc(N(c3ccc(-c4ccc5c(c4)c4ccccc4n5-c4ccccc4)cc3)c3ccc4ncccc4c3)cc21]

Compound 4e was obtained in accordance with the general rule, based on 3-(4-bromophenyl)-9-phenyl-9H-carbazole (398 mg, 1 mmol), 9,9-dimethyl-9H-fluorene-2-amine (209 mg, 1 mmol) and 6-chloroquinoline (182 mg, 1.10 mmol) as second aryl halide X-C. The compound was obtained as a yellow solid (595 mg, 0.91 mmol, 91%) using column chromatography (hexane:ethyl acetate 2:1). Melting point: 168-169° C. $^1$H NMR (400 MHz, DMSO-$d_6$) δ=8.74 (dd, J=4.3 Hz, 1.8 Hz, 1H), 8.58 (d, J=1.5 Hz, 1H), 8.33 (d, J=7.8 Hz, 1H), 8.14 (m, 1H), 7.93 (m, 1H), 7.78-7.60 (m, 9H), 7.56-7.47 (m, 4H), 7.45-7.35 (m, 5H), 7.34-7.20 (m, 5H), 7.08 (dd, J=8.3 Hz, 2.0 Hz, 1H), 1.37 ppm (s, 6H); $^{13}$C NMR (101 MHz, DMSO-$d_6$) δ=155.0, 153.2, 148.7, 146.3, 145.7, 145.4, 144.6, 140.5, 139.4, 138.2, 136.8, 135.8, 134.7, 134.4, 131.8, 130.2 (2C), 130.1, 129.0, 127.8 (2C), 127.6, 127.1, 126.8, 126.8, 126.6 (2C), 126.4, 124.9, 124.5 (2C), 123.6, 123.4, 122.9, 122.7, 121.7, 121.2, 120.8, 120.1, 119.6, 118.9, 118.3, 118.2, 110.0, 109.7, 46.7, 26.7 ppm (20); IR v=1599 (m), 1497 (s), 1474 (s), 1458 (vs), 1448 (vs), 1299 (s), 1231 (vs), 758 (s), 735 (vs), 696 cm$^{-1}$ (s); CHN: calculated (%) for $C_{48}H_{35}N_3$: C, 88.18, H, 5.40, N, 6.43; detected: C, 88.06, H, 5.62, N, 6.20.

Example 5e: Preparation of Compound 4f

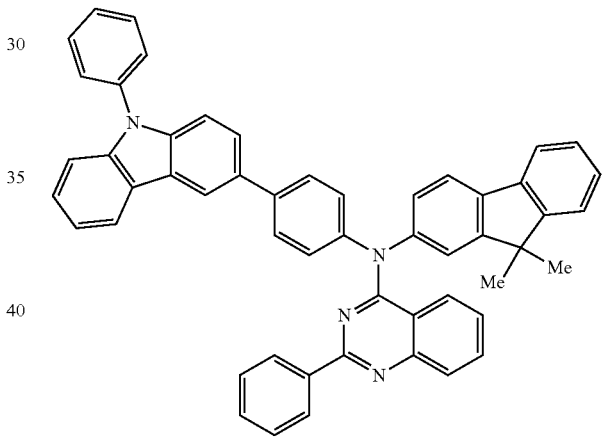

Compound 4f was obtained in accordance with the general rule, starting with 3-(4-bromophenyl)-9-phenyl-9H-carbazole (398 mg, 1 mmol), 9,9-dimethyl-9H-fluorene-2-amine (209 mg, 1 mmol) and 4-chloro-2'-phenylquinazoline (273 mg, 1.10 mmol) as second aryl halide X-C. The compound was obtained as a yellow solid (549 mg, 0.75 mmol, 75%) using column chromatography (hexane:ethyl acetate 4:1). Melting point: 206-207° C. $^1$H NMR (400 MHz, DMSO-$d_6$) δ=8.67 (d, J=1.5 Hz, 1H), 8.36 (d, J=7.8 Hz, 1H), 8.23 (dd, J=8.0 Hz, 1.8 Hz, 2H), 7.95 (d, J=8.0 Hz, 1H), 7.85 (dd, J=8.3 Hz, 5.3 Hz, 3H), 7.82-7.52 (m, 10H), 7.46-7.23 (m, 13H), 7.14 (dd, J=8.2 Hz, 1.9 Hz, 1H), 1.38 ppm (s, 6H); $^{13}$C NMR (101 MHz, DMSO-$d_6$) δ=162.7, 158.7, 154.6, 153.5, 152.9, 145.9, 145.3, 140.6, 139.6, 138.0, 137.8, 137.7, 136.7, 135.9, 133.0, 131.4, 130.4, 130.2 (2C), 128.7, 128.3, 127.8 (2C), 127.7 (3C), 127.2, 127.1, 126.7 (2C), 126.6, 126.6 (2C), 126.5, 125.8, 125.5, 125.0, 124.9, 123.5, 122.9, 122.8, 121.2, 121.0, 120.9, 120.2, 120.0, 118.5, 116.4, 110.0, 109.7, 46.5, 26.6 ppm (20); IR v=1484 (vs), 1474 (vs), 1457 (s), 1375 (vs), 1331 (vs), 1232 (s), 759 (vs), 736 (vs), 707 (vs), 698 cm$^{-1}$ (vs); CHN:

calculated (%) for C₅₃H₃₈N₄: C, 87.09, H, 5.24, N, 7.67; detected: C, 86.78, H, 5.48, N, 7.55.

Example 5f: Preparation of Compound 4g

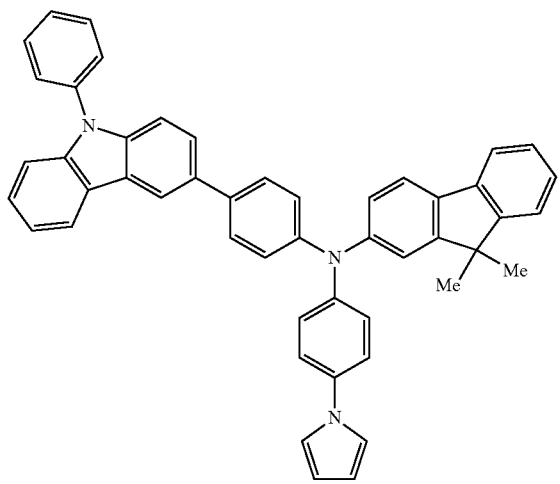 [SMILES: CC1(C)c2ccccc2-c2ccc(N(c3ccc(-c4ccc5c(c4)c4ccccc4n5-c4ccccc4)cc3)c3ccc(-n4cccc4)cc3)cc21]

Compound 4g was obtained in accordance with the general rule, starting with 3-(4-bromophenyl)-9-phenyl-9H-carbazole (398 mg, 1 mmol), 9,9-dimethyl-9H-fluorene-2-amine (209 mg, 1 mmol) and 1-(4-chlorophenyl)-1H-pyrrole (199 mg, 1.10 mmol) as second aryl halide X-C. The compound was obtained as a colorless solid (633 mg, 0.95 mmol, 95%) using column chromatography (hexane:ethyl acetate 9:1). Melting point: 173-174° C. ¹H NMR (400 MHz, DMSO-d₆) δ=8.57 (d, J=1.5 Hz, 1H), 8.34 (d, J=7.5 Hz, 1H), 7.77-7.62 (m, 9H), 7.57-7.48 (m, 4H), 7.47-7.37 (m, 3H), 7.34-7.24 (m, 6H), 7.16 (d, J=8.8 Hz, 4H), 7.03 (dd, J=8.2 Hz, 2.1 Hz, 1H), 6.25 (t, J=2.1 Hz, 2H), 1.39 ppm (s, 6H); ¹³C NMR (101 MHz, DMSO-d₆) δ=154.9, 153.2, 146.6, 146.0, 144.6, 140.6, 139.4, 138.3, 136.8, 135.3, 135.1, 133.9, 132.0, 130.2 (2C), 127.7 (2C), 127.7, 127.1, 126.7, 126.6 (2C), 126.5, 124.9 (2C), 123.7 (2C), 123.4, 123.0, 122.9, 122.7, 121.2, 120.8, 120.6 (2C), 120.2, 119.6, 118.9 (2C), 118.2, 118.2 (2C), 110.3 (2C), 110.0, 109.7, 46.5, 26.8 ppm (2C); IR v=1599 (w), 1512 (vs), 1501 (s), 1449 (s), 1311 (m), 1232 (m), 1069 (m), 735 (s), 723 (vs), 698 cm⁻¹ (s); CHN: calculated (%) for C₄₉H₃₇N₃: C, 88.12, H, 5.58, N, 6.29; detected: C, 88.07, H, 5.75, N, 6.19.

Example 5g: Preparation of Compound 4h

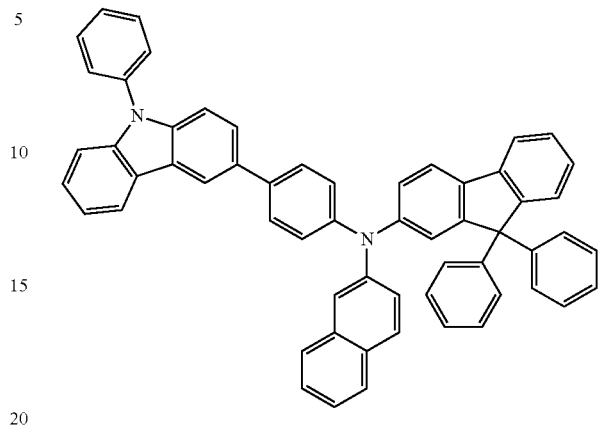

Compound 4h was obtained in accordance with the general rule, starting with 3-(4-bromophenyl)-9-phenyl-9H-carbazole (398 mg, 1 mmol), 9,9-diphenyl-9H-fluorene-2-amine (333 mg, 1 mmol) and 2-bromonaphthaline (230 mg, 1.10 mmol) as second aryl halide X-C. The compound was obtained as a beige solid (743 mg, 0.96 mmol, 96%) using column chromatography (hexane:ethyl acetate 9:1). Melting point: 185-186° C. ¹H NMR (400 MHz, DMSO-d₆) δ=8.48 (s, 1H), 8.27 (d, J=7.5 Hz, 1H), 7.77-7.65 (m, 4H), 7.61-7.47 (m, 8H), 7.47-7.40 (m, 2H), 7.38-7.20 (m, 8H), 7.19-6.95 ppm (m, 16H); ¹³C NMR (101 MHz, DMSO-d₆) δ=151.9, 150.3, 146.9, 145.5, 145.3 (2C), 144.6, 140.5, 139.4 (2C), 136.7, 135.8, 134.5, 133.9, 131.8, 130.1 (2C), 129.7, 129.7, 129.0, 128.2 (40), 127.6 (br, s, 60), 127.4, 127.0, 126.8, 126.6 (2C), 126.5 (30), 126.4 (2C), 125.9, 124.8, 124.6, 124.5 (2C), 123.8, 123.4, 123.0, 122.9, 121.5, 121.1, 120.7, 120.1, 119.8, 119.6, 118.1, 109.9, 109.7, 64.8 ppm; IR v=1596 (m), 1501 (m), 1474 (m), 1452 (s), 1295 (m), 1281 (m), 1231 (m), 805 (m), 743 (vs), 696 cm⁻¹ (vs); CHN: calculated (%) for O₅₀H₄₀N₂: C, 91.21, H, 5.19, N, 3.61; detected: C, 91.07, H, 5.45, N, 3.47.

Example 5h: Preparation of Compound 4i

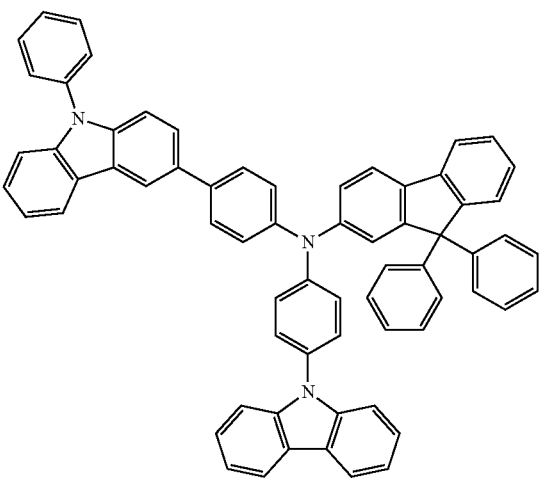 [SMILES: c1ccc(-n2c3ccccc3c3cc(-c4ccc(N(c5ccc(-n6c7ccccc7c7ccccc76)cc5)c5ccc6c(c5)C(c5ccccc5)(c5ccccc5)c5ccccc5-6)cc4)ccc32)cc1]

Compound 4i was obtained in accordance with the general rule, starting with 3-(4-bromophenyl)-9-phenyl-9H-carbazole (398 mg, 1 mmol), 9,9-diphenyl-9H-fluorene-2-amine (333 mg, 1 mmol) and 9-(4-bromophenyl)-9H-carbazole (414 mg, 1.10 mmol) as second aryl halide X-C. The compound was obtained as a beige solid (849 mg, 0.95 mmol, 95%) using column chromatography (hexane:ethyl acetate 4:1). Melting point: 192-193° C. $^1$H NMR (400 MHz, DMSO-d$_6$) δ=8.45 (s, 1H), 8.23 (d, J=7.8 Hz, 1H), 8.16 (d, J=7.8 Hz, 2H), 7.76-7.53 (m, 9H), 7.48-7.35 (m, 12H), 7.34-7.14 ppm (m, 20H); $^{13}$C NMR (101 MHz, DMSO-d$_6$) δ=153.8, 152.0, 148.3, 147.8, 146.9, 146.9 (2C), 142.2, 141.9 (2C), 141.0, 140.8, 138.7, 137.8, 136.2, 133.7, 132.6, 130.7 (2C), 129.1 (4C), 129.0 (40), 129.0, 128.7 (2C), 128.4, 128.2, 128.0 (2C), 127.9, 127.5 (2C), 127.1, 127.0, 126.7 (2C), 125.8 (2C), 125.8 (2C), 125.3 (2C), 124.9, 124.6, 124.4, 124.1 (2C), 123.2, 122.0, 121.2, 121.1 (2C), 121.0, 120.6 (2C), 120.6, 119.1, 110.9, 110.7, 110.6 (2C), 66.4; IR v=1598 (m), 1509 (s), 1475 (1451 vs), 1306 (m), 1286 (m), 1232 (m), 747 (vs), 724 (s), 699 cm$^{-1}$ (s); CHN: calculated (%) for $C_{67}H_{45}N_3$: C, 90.21, H, 5.08, N, 4.71; detected: C, 89.99, H, 5.18, N, 4.72.

The invention claimed is:

1. A single pot method for the selective arylation of a primary aromatic amine with the formula A-NH$_2$ to yield a tertiary aromatic N-ABC amine, wherein the moieties A, B and C are independently of one another the same or different substituted or unsubstituted aromatic moieties, at least one of the moieties A, B or C has a biphenyl unit, comprising the steps
reacting the primary aromatic amine having the formula A-NH$_2$ with an aromatic compound of formula X-B, wherein X is a halogen or a trifluoromethylsulfonic acid moiety, in the presence of a first palladium complex catalyst and a base at a first reaction temperature for a time to obtain a secondary amine having a formula A-NH-B;
reacting the secondary amine with an aromatic compound of formula X-C at a second reaction temperature, which is higher than the first reaction temperature, for a time sufficient to form the tertiary aromatic N-ABC amine, wherein X is a halogen or a trifluoromethylsulfonic acid moiety, in the presence of a second palladium complex catalyst and a base;
wherein the second reaction temperature is in the range of about 90° C. to 144° C. and the first reaction temperature is in the range of about 30° C. to 80° C. and the first catalyst and the second catalyst are bis(diisopropylphosphino)ferrocene palladium complexes.

2. Method according to claim 1, wherein at least two of the aromatic substituents A, B or C have a biphenyl unit which may be the same or different from each other.

3. Method according to claim 1, wherein the biphenyl unit is directly bonded to the secondary nitrogen atom of the amine.

4. Method according to claim 1, wherein the biphenyl unit is a bridged biphenyl unit of formula 2 or 3

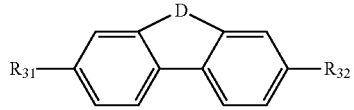

Formula 2

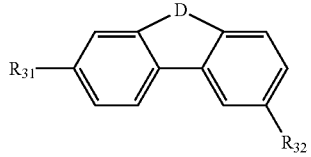

Formula 3 wherein D may be oxygen, sulfur or carbon, and in the case of nitrogen may be substituted once, or in the case of carbon can be substituted twice with methyl, ethyl, biphenyl, naphthyl or phenyl, R31 may be hydrogen, phenyl, biphenyl or pyridyl, R32 may be a leaving group, halogen, a primary amine group NH$_2$ or a trifluoromethylsulfonic acid moiety, depending on whether the moiety is used as A, B or C; or R32 is a spacer which is arranged between A, or B or C and X or NH$_2$.

5. Method according to claim 1, wherein the biphenyl unit is 2-fluorene, 3-fluorene, 2-(9,9-diphenylfluorene), 2-(9,9-dimethylfluorene), 3-(9,9-diphenylfluorene), 3-(9,9-dimethylfluorene), 3-(4-phenyl)-9-phenyl-9H-carbazole, 3-(4-phenyl)-9-methyl-9H-carbazole, 3-(4-phenyl)-9-biphenyl-9H-carbazole, 2-(4-phenyl)-9-phenyl-9H-carbazole, 2-(4-phenyl)-9-methyl-9H-carbazole, 2-(4-phenyl)-9-biphenyl-9H-carbazole, 3-(4-biphenyl)-9-phenyl-9H-carbazole, 3-(4-biphenyl)-9-methyl-9H-carbazole, 3-(4-biphenyl)-9-biphenyl-9H-carbazole, 2-(4-biphenyl)-9-phenyl-9H-carbazole, 2-(4-biphenyl)-9-methyl-9H-carbazole, 2-(4-biphenyl)-9-biphenyl-9H-carbazole, 3-(9-phenyl-9H-carbazole), 3-(9-methyl-9H-carbazole), 3-(9-biphenyl-9H-carbazole), 2-(9-phenyl-9H-carbazole), 2-(9-methyl-9H-carbazole), 2-(9-biphenyl-9H-carbazole) or triphenylene.

6. Method according to claim 1, wherein each palladium complex is a solid, solution or powder mixture.

7. Method according to claim 1, wherein each palladium atom of the catalytic complex is additionally complexed by 2,4,6,8-tetramethylcyclotetrasiloxane, bis(dibenzylideneacetone) or maleimide.

8. Method according to claim 1, wherein each palladium atom in the palladium catalytic complex is complexed by 1,1'-bis(diisopropylphosphino)ferrocene.

9. Method according to claim 1, containing the steps:
providing the primary aromatic amine A-NH$_2$, the aryl halide X-B, and a suitable solvent and, optionally, a bis(diisopropylphosphino)ferrocene in a reaction vessel;
adding a palladium complex, in which the palladium atom is complexed by at least one bis(diisopropylphosphino)ferrocene ligand, in the form of a solid or a solution to form a reaction mixture;
heating the reaction mixture thus obtained in the reaction vessel;
separating off the reaction product, a secondary aromatic amine A-NH-B; and,
where applicable, cleaning the secondary aromatic amine A-NH-B.

10. Method according to claim 1, containing the steps:
providing the primary aromatic amine A-NH$_2$, the aryl halide X-B, and a suitable solvent and, optionally, a bis(diisopropylphosphino)ferrocene in a reaction vessel;
adding a palladium complex, in which the palladium atom is complexed by at least one bis(diisopropylphosphino)ferrocene ligand, in the form of a solid or a solution to form a reaction mixture;

heating the reaction mixture thus obtained to the first reaction temperature;

adding an aryl halide X-C;

heating to the second reaction temperature; and separating off and, where applicable, cleaning the tertiary aromatic amine N-ABC.

11. Method according to claim 1, wherein the second reaction temperature is in the range of about 100° C. to 144° C. and the first reaction temperature is in the range of about 30° C. to 80° C.

12. Method according to claim 1, wherein the second reaction temperature is in the range of about 100° C. to 139° C. and the first reaction temperature is in the range of about 50° C. to 80° C.

* * * * *